United States Patent
Houhou et al.

(10) Patent No.: US 10,370,444 B2
(45) Date of Patent: *Aug. 6, 2019

(54) PROPHYLAXIS OF COLORECTAL AND GASTROINTESTINAL CANCER

(71) Applicants: LES LABORATOIRES SERVIER, Suresnes (FR); INSTITUT NATIONAL DE LA SANTÉ ET DE LA RECHERCHE MÉDICALE (INSERM), Paris (FR); CENTRE NATIONAL DE LA RECHERCHE SCIENTIFIQUE (CNRS), Paris (FR)

(72) Inventors: Leila Houhou, Montpellier (FR); Mathieu Petremann, Montpellier (FR); Dominique Joubert, Sète (FR); Frédéric Hollande, Les Matelles (FR)

(73) Assignees: Les Laboratoires Servier, Suresnes (FR); Institut National de la Santé et de la Recherche Médicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/278,246

(22) Filed: Sep. 28, 2016

(65) Prior Publication Data

US 2017/0233469 A1 Aug. 17, 2017

Related U.S. Application Data

(63) Continuation of application No. 14/233,593, filed as application No. PCT/EP2011/001448 on Mar. 23, 2011, now abandoned.

(60) Provisional application No. 61/317,245, filed on Mar. 24, 2010.

(51) Int. Cl.
| | |
|---|---|
| *A61K 39/395* | (2006.01) |
| *C07K 16/26* | (2006.01) |
| *G01N 33/574* | (2006.01) |
| *A61K 45/06* | (2006.01) |
| *C07K 16/30* | (2006.01) |
| *G01N 33/74* | (2006.01) |
| *A61K 39/00* | (2006.01) |

(52) U.S. Cl.
CPC ........ *C07K 16/26* (2013.01); *A61K 39/39558* (2013.01); *A61K 45/06* (2013.01); *C07K 16/3046* (2013.01); *G01N 33/57419* (2013.01); *G01N 33/57488* (2013.01); *G01N 33/74* (2013.01); *A61K 2039/505* (2013.01); *C07K 2317/24* (2013.01); *C07K 2317/33* (2013.01); *C07K 2317/34* (2013.01); *C07K 2317/565* (2013.01); *C07K 2317/76* (2013.01); *C07K 2317/92* (2013.01); *G01N 2333/5758* (2013.01); *G01N 2333/595* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,854,932 B2 | 12/2010 | Singh | |
| 9,217,032 B2 | 12/2015 | Pannequin | |
| 9,611,320 B2 * | 4/2017 | Pannequin | ............. C07K 16/26 |
| 2001/0039017 A1 | 11/2001 | Waldman | |
| 2003/0021786 A1 | 1/2003 | Gevas | |
| 2007/0248608 A1 | 10/2007 | Grimes | |
| 2008/0187577 A1 | 8/2008 | Singh | |
| 2009/0275546 A1 | 11/2009 | Signore | |
| 2011/0318380 A1 | 12/2011 | Brix | |

FOREIGN PATENT DOCUMENTS

| | | |
|---|---|---|
| WO | WO 2004/090547 A2 | 10/2004 |
| WO | WO 2006/032980 A1 | 3/2006 |
| WO | WO 2007/135542 A2 | 11/2007 |
| WO | WO 2008/076454 A1 | 6/2008 |
| WO | WO 2009/099649 A1 | 8/2009 |
| WO | WO 2011/045080 A2 | 4/2011 |
| WO | WO 2011/083088 A2 | 7/2011 |
| WO | WO 2011/104338 * | 9/2011 |

OTHER PUBLICATIONS

Bismuth et al., 1996 "Resection of Nonresectable Liver Metastases from Colorectal Cancer After Neoadjuvant Chemotherapy," *Annals of Surgery* 224(4):509-520.

Caplin et al., 1999 "Expression and processing of gastrin in hepatocellular carcinoma, fibrolamellar carcinoma and cholangiocarcinoma," *Journal of Hepatology* 30:519-526.

(Continued)

*Primary Examiner* — Sheela J. Huff

(74) *Attorney, Agent, or Firm* — Buchanan Ingersoll & Rooney PC

(57) ABSTRACT

The present disclosure provides methods and compositions useful for preventing gastrointestinal and/or colorectal cancer in animals, including humans, having pre-cancerous adenomatous polyps. The present disclosure provides compositions comprising anti-PG antibodies suitable for use in the methods of the disclosure. The present disclosure also provides methods and compositions useful for monitoring the efficacy of anti-PG treatment in subjects with pre-cancerous polyps.

8 Claims, 39 Drawing Sheets

Specification includes a Sequence Listing.

(56) References Cited

OTHER PUBLICATIONS

Ciccotosto et al., 1995, "Expression Processing, and Secretion of Gastrin in Patients With Colorectal Carcinoma," *Gastroenterology* 109(4):1142-1153.

Hecht, 2008, "Current and Emerging Therapies for Metastatic Colorectal Cancer: Applying Research Findings to Clinical Practice," *Am. Journal of Health-System Pharmacy* 65(11):S15-S24 (suppl. 4).

Hollande et al., 2003, "Adherens Junctions and Tight Junctions Are Regulated Via Different Pathways by Progastrin in Epithelial Cells," *J. Cell Science* 116(7):1187-1197.

Jean et al., 2008, "Epidermal Growth Factor Receptor Monoclonal Antibodies for the Treatment of Metastatic Colorectal Cancer," *Pharmacotherapy* 28(6):742-754.

Pannequin et al., 2007, "β-Catenin/Tcf-4 Inhibition After Progastrin Targeting Reduces Growth and Drives Differentiation of Intestinal Tumors," *Gastroenterology* 133(5):1554-1568.

Petkova et al., 2006, "Enhanced half-life of genetically engineered human IgG1 antibodies in a humanized FcRn mouse model: potential application in humorally mediated autoimmune disease," *International Immunology* 18(12):1759-1769.

Rengifo-Cam et al., 2004 "Role of Progastrins and Gastrins and Their Receptors in GI and Pancreatic Cancers: Targets for Treatment," *Current Pharmaceutical Design* 10:2345-5358.

Siddheshwar et al., 2001, "Plasma Levels of Progastrin But Not Amidated Gastrin or Glycine Extended Gastrin are Elevated in Patients With Colorectal Carcinoma," *Gut* 48(1):47-52.

Singh et al., 1996, "Gastrin Gene Expression is Required for the Proliferation and Tumorigenicity of Human Colon Cancer Cells," *Cancer Research* 56(18):4111-4115.

Singh et al., 2000, "Mice Overexpressing Progastrin Are Predisposed for Developing Aberrant Colonic Crypt Foci in Response to AOM," *Am. Journal of Physiology* 278(3):G390-G399.

Singh et al., 2000, "Progastrin Expression Predisposes Mice to Colon Carcinomas and Adenomas in Response to a Chemical Carcinogen," *Gastroenterology* 119(1):162-171.

Singh et al., 2007, "Development of Progastrin (PG) Specific Monoclonal Antibodies (Mabs) and PG Specific Vaccine for Attenuating Growth Factor Effects of Autocrine and Endocrine PG-Like Pepticles on Colon Cancer Cells and Colon Carcinogenesis, respectively," *Proceedings of the American Association for Cancer Research Annual Meeting* (Apr. 2007, vol. 48, p. 845) and *98th Annual Meeting of the American Association for Cancer Research*, Los Angeles, CA (Abstract).

Smith et al., 2006 "Basic-Alimentary Tract—Production, Secretion, and Biological Activity of the C-Terminal Flanking Peptide of Human Progastrin," *Gastroenterology* 131(5):1463-1474.

Tamiya et al., 2009, "Safety of Bevacizumab Treatment in Combination With Standard Chemotherapy for Metastatic Colorectal Cancer: A Retrospective Review of 65 Japanese Patients," *Intl. J. Clin. Oncology* 14(6):513-517.

Watson et al., 1999 "A Comparison of an Anti-Gastrin Antibody and Cytotoxic Drugs in the Therapy of Human Gastric Ascites in SCID Mice," *Int. J. Cancer* 81:248-254.

Wicha et al., 2006 "Cancer Stem Cells: An Old Idea—A Paradigm Shift," *Cancer Res* 66(4):1883-1890.

Partial International Search Report from related International Application No. PCT/EP2011/000046 dated Apr. 15, 2011.

International Search Report and Written Opinion for related International Application No. PCT/EP2011/001448, dated Jun. 9, 2011.

International Search Report from related International Application No. PCT/EP2011/000046 dated Aug. 26, 2011.

Balmana et al., 2009 "BRCA in breast cancer: ESMO Clinical Recommendations," Annals of Oncology 20(Supp4):iv19-20.

Brand et al., 2006 "Prospect for Anti-HER2 Receptor Therapy in Breast Cancer," *Anticancer Res* 26:463-470.

Casset et al., 2003 "A peptide mimetic of an anti-CD4 monoclonal antibody by rational design," *Biochem Biophys Res Commun* 307:198-205.

George et al., 1998 "Differential Effects of Anti-$\beta_2$-Glycoprotein I Antibodies on Endothelial Cells and on the Manifestations of Experimental Antibphospholipid Syndrome," *Circulation* 97:900-906.

Kataj A et al., 2009 "Primary breast cancer: ESMO Clinical Recommendations for diagnosis, treatment and follow-up," *Annals of Oncology* 20(Supp4):iv10-iv14.

Nelson et al., 2009 "Screening for Breast Cancer: An Update for the U.S. Preventive Services Task Force," *Annals of Internal Medicine* 151(10):727-737.

Paul, 1993 *Fundamental Immunology*, $3^{rd}$ Edition pp. 292-295.

Pascalis et al., 2002 "Grafting of 'Abbreviated' Complementarity-Determining Regions Containing Specificity-Determining Residues Essential for Ligand Contact to Engineer a Less Immunogenic Humanized Monoclonal Antibody," *J Immunol* 169:376-3084.

Rudikoff et al., 1979 "Single amino acid substitution altering antigen-binding specificity," *Proc. Natl. Adad. Sci. USA* 79:1979-1983.

Strome et al., 2007 "A Mechanistic Perspective of Monoclonal Antibodies in Cancer Therapy Beyong Target-Related Effects," *The Oncologist* 12:1084-1095.

* cited by examiner

FIG. 1

```
Preprogastrin:  M QRLCVYVLIF ALALAAFSEA SWKPRSQQPD APLGTGANRD LELPWLEQQG
               -21         -11         -1         11         21
                PASHHRRQLG PQGPPHLVAD PSKKQGPWLE EEEEAYGWMD FGRRSAEDEN
                31         41         51         61         71

Progastrin:                           SWKPRSQQPD APLGTGANRD LELPWLEQQG
                                      +1         11         21
                PASHHRRQLG PQGPPHLVAD PSKKQGPWLE EEEEAYGWMD FGRRSAEDEN
                31         41         51         61         71

G34:               QLG PQGPPHLVAD PSKKQGPWLE EEEEAYGWMD F-NH₂
                       41         51         61         71

G34-Gly:           QLG PQGPPHLVAD PSKKQGPWLE EEEEAYGWMD FG
                       41         51         61         71

G17:                                QGPWLE EEEEAYGWMD F-NH₂
                                           61         71

G17-Gly:                            QGPWLE EEEEAYGWMD FG
                                           61         71

CTFP:                                                     SAEDEN
                                                          75
```

FIG. 2A mV$_H$ MAb3

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
                20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
            35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
        50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
            100                 105                 110 gtc tcc tca                                                       345
Val Ser Ser
        115
```

FIG. 2B mV$_L$ MAb3

```
gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
                20                  25              30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
            35                  40              45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
        50                  55              60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65              70                  75                  80 agc aga ctg gag gct gag gat ctg gga gtt tat tac tgc ttt caa ggt     288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa     336
Ser His Val Pro Phe Thr Phe Gly Gly Gly Thr Lys Leu Glu Ile Lys
                100                 105                 110
```

FIG. 2C mV$_H$ MAb4

```
cag gtt cag ttg cag cag tct gga gct gag ctg atg aag cca ggg gcc    48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc    96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
                35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
        50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
            100                 105                 110 ctg gtc act gtc tct gca                                            354
Leu Val Thr Val Ser Ala
            115
```

FIG. 2D mV$_L$ MAb4

| | | | | | | | | | | | | | | | |
|---|---|---|---|---|---|---|---|---|---|---|---|---|---|---|---|
| gat | ctt | gtg | atg | acc | caa | act | cca | ctc | tcc | ctg | cct | gtc | agt | ctt | gga | 48 |
| Asp | Leu | Val | Met | Thr | Gln | Thr | Pro | Leu | Ser | Leu | Pro | Val | Ser | Leu | Gly |
| 1 | | | | 5 | | | | | 10 | | | | | 15 |

| gat | caa | gcc | tcc | atc | tct | tgc | aga | tct | agt | cag | agc | ctt | gta | cac | agt | 96 |
| Asp | Gln | Ala | Ser | Ile | Ser | Cys | Arg | Ser | Ser | Gln | Ser | Leu | Val | His | Ser |
| | | | 20 | | | | | 25 | | | | | 30 |

| agt | gga | gtc | acc | tat | tta | cat | tgg | tac | ctg | cag | aag | cca | ggc | cag | tct | 144 |
| Ser | Gly | Val | Thr | Tyr | Leu | His | Trp | Tyr | Leu | Gln | Lys | Pro | Gly | Gln | Ser |
| | | | 35 | | | | | 40 | | | | | 45 |

| cca | aag | ctc | ctg | atc | tac | aaa | gtt | tcc | aac | cga | ttt | tct | ggg | gtc | cca | 192 |
| Pro | Lys | Leu | Leu | Ile | Tyr | Lys | Val | Ser | Asn | Arg | Phe | Ser | Gly | Val | Pro |
| | 50 | | | | | 55 | | | | | 60 |

| gac | agg | ttc | agt | ggc | agt | gga | tca | ggg | aca | gat | ttc | aca | ctc | aag | atc | 240 |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |

| agc | aga | gtg | gag | gct | gag | gat | ctg | gga | gtt | tat | ttc | tgc | tct | caa | agt | 288 |
| Ser | Arg | Val | Glu | Ala | Glu | Asp | Leu | Gly | Val | Tyr | Phe | Cys | Ser | Gln | Ser |
| | | | | 85 | | | | | 90 | | | | | 95 |

| aca | cat | gtt | cct | ccc | acg | ttc | ggc | tcg | ggg | aca | aag | ttg | gaa | ata | aaa | 336 |
| Thr | His | Val | Pro | Pro | Thr | Phe | Gly | Ser | Gly | Thr | Lys | Leu | Glu | Ile | Lys |
| | | | | 100 | | | | | 105 | | | | | 110 |

FIG. 2E mV$_H$ MAb8

| | | | | | | | | | | | | | | | | |
|---|---|---|---|---|---|---|---|---|---|---|---|---|---|---|---|---|
| gaa | gtg | cag | ctg | gtg | gag | tct | ggg | gga | ggc | tta | gtg | aag | cct | gga | ggg | 48 |
| Glu | Val | Gln | Leu | Val | Glu | Ser | Gly | Gly | Gly | Leu | Val | Lys | Pro | Gly | Gly | |
| 1 | | | | 5 | | | | | | 10 | | | | | 15 | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | act | ttc | act | acc | tat | 96 |
| Ser | Leu | Lys | Leu | Ser | Cys | Ala | Ala | Ser | Gly | Phe | Thr | Phe | Thr | Thr | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gcc | atg | tct | tgg | gtt | cgc | cag | act | ccg | gag | aag | agg | ctg | gag | tgg | gtc | 144 |
| Ala | Met | Ser | Trp | Val | Arg | Gln | Thr | Pro | Glu | Lys | Arg | Leu | Glu | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | acc | att | agt | agt | ggt | ggt | act | tac | acc | tac | tat | cca | gac | agt | gtg | 192 |
| Ala | Thr | Ile | Ser | Ser | Gly | Gly | Thr | Tyr | Thr | Tyr | Tyr | Pro | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggt | cga | ttc | acc | atc | tcc | aga | gac | aat | gcc | aag | aac | gcc | cta | tac | 240 |
| Lys | Gly | Arg | Phe | Thr | Ile | Ser | Arg | Asp | Asn | Ala | Lys | Asn | Ala | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | agc | agt | ctg | agg | tct | gag | gac | acg | gcc | atg | tat | tac | tgt | 288 |
| Leu | Gln | Met | Ser | Ser | Leu | Arg | Ser | Glu | Asp | Thr | Ala | Met | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aca | cag | ggg | aat | tac | tct | ttg | gac | ttc | tgg | ggc | caa | ggc | acc | tct | 336 |
| Ala | Thr | Gln | Gly | Asn | Tyr | Ser | Leu | Asp | Phe | Trp | Gly | Gln | Gly | Thr | Ser | |
| | | | 100 | | | | | 105 | | | | | 110 | | | |

| | | | | | |
|---|---|---|---|---|---|
| ctc | aca | gtc | tcc | tca | 351 |
| Leu | Thr | Val | Ser | Ser | |
| | | 115 | | | |

FIG. 2F mV$_L$ MAb8

```
gac att gtg atg acg cag gct gca tcc tct aat cca gtc act ctt gga    48
Asp Ile Val Met Thr Gln Ala Ala Ser Ser Asn Pro Val Thr Leu Gly
1             5                   10                  15 aca tcc gct tcc atc tcc tgc agg tct agt aag agt ctc cga cat act    96
Thr Ser Ala Ser Ile Ser Cys Arg Ser Ser Lys Ser Leu Arg His Thr
                20              25              30 aaa ggc atc act ttt ttg tat tgg tat ctg cag aag cca ggc cag tct   144
Lys Gly Ile Thr Phe Leu Tyr Trp Tyr Leu Gln Lys Pro Gly Gln Ser
            35              40                  45 cct cag ctc ctg att tat cag atg tcc aac ctt gcc tca gga gtc cca   192
Pro Gln Leu Leu Ile Tyr Gln Met Ser Asn Leu Ala Ser Gly Val Pro
        50              55                  60 gac agg ttc agt agc agt ggg tca gga act gat ttc aca ctg aga atc   240
Asp Arg Phe Ser Ser Ser Gly Ser Gly Thr Asp Phe Thr Leu Arg Ile
65              70              75                  80 agc aga gtg gag gct gag gat ttg ggt gtt tat tac tgt gct caa aat   288
Ser Arg Val Glu Ala Glu Asp Leu Gly Val Tyr Tyr Cys Ala Gln Asn
                85              90              95 cta gaa ctt ccg ctc acg ttc ggt gct ggg acc aag ctg gag ctg aaa   336
Leu Glu Leu Pro Leu Thr Phe Gly Ala Gly Thr Lys Leu Glu Leu Lys
            100             105             110
```

FIG. 2G mV$_H$ MAb13

```
gag gtg cag ctg gtg gag tct ggg gga ggc ttg gtg cag cct gga ggg    48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat    96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc   144
Gly Met Ser Trp Val Arg Gln Ser Pro Asp Arg Arg Leu Glu Leu Val
        35                  40                  45 gca agt att aat act ttt ggt gat aga acc tat tat cca gac agt gtg   192
Ala Ser Ile Asn Thr Phe Gly Asp Arg Thr Tyr Tyr Pro Asp Ser Val
    50                  55                  60 aag ggc cga ttc acc atc tcc aga gac aat gcc aag aac acc ctg tac   240
Lys Gly Arg Phe Thr Ile Ser Arg Asp Asn Ala Lys Asn Thr Leu Tyr
65              70                  75                  80 ctg caa atg acc agt ctg aag tct gag gac aca gcc att tat tac tgt   288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc   336
Ala Arg Gly Thr Gly Thr Tyr Trp Gly Gln Gly Thr Thr Leu Thr Val
            100                 105                 110 tcc tca                                                            342
Ser Ser
```

FIG. 2H mV$_L$ MAb13

| | | | | | | | | | | | | | | | | |
|---|---|---|---|---|---|---|---|---|---|---|---|---|---|---|---|---|
|gat|gtt|gtg|ctg|acc|cag|act|cca|ctc|act|ttg|tcg|gtt|acc|att|gga|48|
|Asp|Val|Val|Leu|Thr|Gln|Thr|Pro|Leu|Thr|Leu|Ser|Val|Thr|Ile|Gly||
|1|||| 5 |||||10||||| 15 |||

| | | | | | | | | | | | | | | | | |
|---|---|---|---|---|---|---|---|---|---|---|---|---|---|---|---|---|
|caa|cca|gcc|tcc|atc|tcc|tgc|aag|tca|agt|cag|agc|ctc|tta|gat|agt|96|
|Gln|Pro|Ala|Ser|Ile|Ser|Cys|Lys|Ser|Ser|Gln|Ser|Leu|Leu|Asp|Ser||
||||20||||| 25 |||| 30 ||||

| | | | | | | | | | | | | | | | | |
|---|---|---|---|---|---|---|---|---|---|---|---|---|---|---|---|---|
|gat|gga|aag|aca|tat|ttg|aat|tgg|ttg|tta|cag|agg|cca|ggc|cag|tct|144|
|Asp|Gly|Lys|Thr|Tyr|Leu|Asn|Trp|Leu|Leu|Gln|Arg|Pro|Gly|Gln|Ser||
|||| 35 |||| 40 ||||| 45 ||||

| | | | | | | | | | | | | | | | | |
|---|---|---|---|---|---|---|---|---|---|---|---|---|---|---|---|---|
|cca|aag|cgc|cta|atc|tat|ctg|gtg|tct|aaa|ctg|gac|tct|gga|gtc|cct|192|
|Pro|Lys|Arg|Leu|Ile|Tyr|Leu|Val|Ser|Lys|Leu|Asp|Ser|Gly|Val|Pro||
||| 50 |||| 55 ||||| 60 |||||

| | | | | | | | | | | | | | | | | |
|---|---|---|---|---|---|---|---|---|---|---|---|---|---|---|---|---|
|gac|agg|ttc|act|ggc|agt|gga|tca|ggg|aca|gat|ttc|aca|ctg|aaa|atc|240|
|Asp|Arg|Phe|Thr|Gly|Ser|Gly|Ser|Gly|Thr|Asp|Phe|Thr|Leu|Lys|Ile||
|65|||| 70 ||||| 75 ||||| 80 ||

| | | | | | | | | | | | | | | | | |
|---|---|---|---|---|---|---|---|---|---|---|---|---|---|---|---|---|
|agc|aga|gtg|gag|gct|gag|gat|ttg|gga|gtt|tat|tat|tgc|tgg|caa|ggt|288|
|Ser|Arg|Val|Glu|Ala|Glu|Asp|Leu|Gly|Val|Tyr|Tyr|Cys|Trp|Gln|Gly||
||||| 85 |||||| 90 ||||| 95 ||

| | | | | | | | | | | | | | | | | |
|---|---|---|---|---|---|---|---|---|---|---|---|---|---|---|---|---|
|aca|cat|ttt|cct|cag|acg|ttc|ggt|gga|ggc|acc|aag|ctg|gaa|atc|aaa|336|
|Thr|His|Phe|Pro|Gln|Thr|Phe|Gly|Gly|Gly|Thr|Lys|Leu|Glu|Ile|Lys||
|||||| 100 |||| 105 ||||| 110 ||

FIG. 21 mV$_H$ MAb16

```
cag gtc caa ctg cag cag tct ggg gct gaa ctg gtg aag cct ggg gct    48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac    96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att   144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc   192
Gly Glu Ile Asn Pro Ser Asn Gly Gly Thr Asn Phe Asn Glu Lys Phe
        50                  55                  60 aag agc aag gcc aca ctg act gta gac aaa tcc tcc agc aca gca tac   240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt   288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act   336
Thr Arg Gly Gly Tyr Tyr Pro Phe Asp Tyr Trp Gly Gln Gly Thr Thr
            100                 105                 110 ctc aca gtc tcc tca                                                351
Leu Thr Val Ser Ser
            115
```

FIG. 2J mV$_L$ MAb16

| | | | | | | | | | | | | | | | | |
|---|---|---|---|---|---|---|---|---|---|---|---|---|---|---|---|---|
| gat | gtt | gtg | atg | acc | cag | act | cca | ctc | act | ttg | tcg | gtt | acc | att | ggg | 48 |
| Asp | Val | Val | Met | Thr | Gln | Thr | Pro | Leu | Thr | Leu | Ser | Val | Thr | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgc | cca | gcc | tcc | atc | tct | tgc | aag | tca | agt | cag | agc | ctc | tta | gac | agt | 96 |
| Arg | Pro | Ala | Ser | Ile | Ser | Cys | Lys | Ser | Ser | Gln | Ser | Leu | Leu | Asp | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gga | aag | aca | tat | ttg | tat | tgg | ttg | tta | cag | agg | cca | ggc | cag | tct | 144 |
| Asp | Gly | Lys | Thr | Tyr | Leu | Tyr | Trp | Leu | Leu | Gln | Arg | Pro | Gly | Gln | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | aag | cgc | cta | atc | tat | ctg | gtg | tct | gag | ctg | gac | tct | gga | gtc | cct | 192 |
| Pro | Lys | Arg | Leu | Ile | Tyr | Leu | Val | Ser | Glu | Leu | Asp | Ser | Gly | Val | Pro | |
| | | | 50 | | | | | 55 | | | | | 60 | | | |

| | | | | | | | | | | | | | | | | |
|---|---|---|---|---|---|---|---|---|---|---|---|---|---|---|---|---|
| gac | agg | atc | act | ggc | agt | ggg | tcg | ggg | aca | gat | ttc | aca | ctg | aag | atc | 240 |
| Asp | Arg | Ile | Thr | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | ttg | gga | gtt | tat | tat | tgc | tgg | caa | gga | 288 |
| Ser | Arg | Val | Glu | Ala | Glu | Asp | Leu | Gly | Val | Tyr | Tyr | Cys | Trp | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | cat | tct | ccg | tac | acg | ttc | gga | ggg | ggg | acc | aag | ctg | gaa | ata | aaa | 336 |
| Thr | His | Ser | Pro | Tyr | Thr | Phe | Gly | Gly | Gly | Thr | Lys | Leu | Glu | Ile | Lys | |
| | | | 100 | | | | | 105 | | | | | 110 | | | |

FIG. 2K mV$_H$ MAb19

```
gat gtg cag ctt cag gag tcg gga cct ggc ctg gtg aaa cct tct cag      48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat      96
Ser Leu Ser Leu Thr Cys Thr Val Thr Gly Tyr Ser Ile Thr Ser Asp
            20                  25                  30 tat gcc tgg aat tgg atc cgg cag ttt cca gga aac aaa ctg gag tgg     144
Tyr Ala Trp Asn Trp Ile Arg Gln Phe Pro Gly Asn Lys Leu Glu Trp
            35                  40                  45 atg ggc tac ata agc ttc agt ggt tac act agt tac aac cca tct ctc     192
Met Gly Tyr Ile Ser Phe Ser Gly Tyr Thr Ser Tyr Asn Pro Ser Leu
        50                  55                  60 aaa agt cga atc tct gtc act cgg gac aca tcc agg aac caa ttc ttc     240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt     288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc     336
Ala Arg Glu Val Asn Tyr Gly Asp Ser Tyr His Phe Asp Tyr Trp Gly
            100                 105                 110 caa ggc acc att gtc aca gtc tcc tca                                  363
Gln Gly Thr Ile Val Thr Val Ser Ser
        115                 120
```

FIG. 2L mV$_L$ MAb19

```
caa ctt gcg ctc act cag tca tct tca gcc tct ttc tcc ctg gga gcc    48
Gln Leu Ala Leu Thr Gln Ser Ser Ser Ala Ser Phe Ser Leu Gly Ala
1                   5                   10                  15 tca gca aaa cta acg tgc act ttg agt agt caa cac aga acg tac acc    96
Ser Ala Lys Leu Thr Cys Thr Leu Ser Ser Gln His Arg Thr Tyr Thr
                20                  25                  30 att gaa tgg tat cag caa cag tca ctc aag cct cct aag tat gtg atg   144
Ile Glu Trp Tyr Gln Gln Gln Ser Leu Lys Pro Pro Lys Tyr Val Met
            35                  40                  45 gag gtt aag aaa gat gga agc cac agc aca ggt cat ggg att cct gat   192
Glu Val Lys Lys Asp Gly Ser His Ser Thr Gly His Gly Ile Pro Asp
        50                  55                  60 cgc ttc tct gga tcc agt tct ggt gct gat cgc tac ctc agc att tcc   240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat   288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc   336
Ala Ile Lys Gly Gln Ser Val Phe Val Phe Gly Gly Gly Thr Lys Val
            100                 105                 110 act gtc cta                                                       345
Thr Val Leu
        115
```

FIG. 3A hV$_H$ MAb3

Gln Val Gln Leu Val Gln Ser Gly Ala Glu Val Lys Lys Pro Gly Ala
1             5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
                100                 105                 110

Val Ser Ser
    115

FIG. 3B hV$_L$ MAb3

Asp Val Val Met Thr Gln Ser Pro Leu Ser Leu Pro Val Thr Leu Gly
1              5                   10                  15

Gln Pro Ala Ser Ile Ser Cys Arg Ser Ser Gln Ser Ile Val His Ser
            20                  25              30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Gly
            85                  90                  95

Ser His Val Pro Phe Thr Phe Gly Gly Gly Thr Lys Val Glu Ile Lys
            100                 105                 110

FIG. 3C hV$_H$ MAb4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
                20              25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
        50                  55                  60

Gln Gly Arg Val Thr Met Thr Arg Asp Thr Ser Thr Ser Thr Val Tyr
65              70                  75                      80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
                100                 105                 110

Leu Val Thr Val Ser Ser
        115

FIG. 3D hV$_L$ MAb4

Asp Ile Val Met Thr Gln Thr Pro Leu Ser Leu Ser Val Thr Pro Gly
1              5                    10                  15

Gln Pro Ala Ser Ile Ser Cys Lys Ser Ser Gln Ser Leu Val His Ser
            20                  25              30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
        50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Pro Thr Phe Gly Gln Gly Thr Lys Leu Glu Ile Lys
            100             105                 110

FIG. 3E hV_H MAb8(a)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
            115
```

FIG. 3F hV$_L$ MAb8(a)

Asp Ile Val Met Thr Gln Ser Pro Leu Ser Leu Pro Val Thr Pro Gly
1         5              10             15

Glu Pro Ala Ser Ile Ser Cys Arg Ser Ser Lys Ser Leu Arg His Thr
            20              25                  30

Lys Gly Ile Thr Phe Leu Tyr Trp Tyr Leu Gln Lys Pro Gly Gln Ser
              35              40              45

Pro Gln Leu Leu Ile Tyr Gln Met Ser Asn Arg Ala Ser Gly Val Pro
        50              55              60

Asp Arg Phe Ser Gly Ser Gly Ser Gly Thr Asp Phe Thr Leu Lys Ile
65              70              75                  80

Ser Arg Val Glu Ala Glu Asp Val Gly Val Tyr Tyr Cys Ala Gln Asn
            85              90              95

Leu Glu Leu Pro Leu Thr Phe Gly Gly Gly Thr Lys Val Glu Ile Lys
              100             105             110

FIG. 3G hV$_H$ MAb8(b)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

FIG. 3H hV$_L$ MAb8(b)

Asp Ile Val Met Thr Gln Ser Pro Leu Ser Leu Pro Val Thr Pro Gly
1        5                  10                 15

Glu Pro Ala Ser Ile Ser Cys Arg Ser Ser Lys Ser Leu Arg His Thr
           20                  25                 30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Leu Thr Phe Gly Gly Gly Thr Lys Val Glu Ile Lys
            100                 105                 110

FIG. 3I hV$_H$ MAb8(c)

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Thr Thr Tyr
20 25 30

Ala Met Ser Trp Val Arg Gln Ala Pro Gly Lys Gly Leu Glu Trp Val
35 40 45

Ser Thr Ile Ser Ser Gly Gly Thr Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Thr Gln Gly Asn Tyr Ser Leu Asp Phe Trp Gly Gln Gly Thr Thr
100 105 110

Val Thr Val Ser Ser
115

FIG. 3J hV$_L$ MAb8(c)

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
                20              25              30

Lys Gly Ile Thr Phe Leu Tyr Trp Tyr Leu Gln Lys Pro Gly Gln Ser
        35                  40              45

Pro Gln Leu Leu Ile Tyr Gln Met Ser Asn Arg Ala Ser Gly Val Pro
        50              55              60

Asp Arg Phe Ser Gly Ser Gly Ser Gly Thr Asp Phe Thr Leu Lys Ile
65              70              75                      80

Ser Arg Val Glu Ala Glu Asp Val Gly Val Tyr Tyr Cys Ala Gln Asn
                85              90                  95

Leu Glu Leu Pro Leu Thr Phe Gly Gly Gly Thr Lys Val Glu Ile Lys
                100         105             110
```

FIG. 3K hV$_H$ MAb13(a)

Glu Val Gln Leu Val Glu Ser Gly Gly Gly Leu Val Gln Pro Gly Gly
1               5                       10                      15

Ser Leu Arg Leu Ser Cys Ala Ala Ser Gly Phe Ile Phe Ser Ser Tyr
            20                  25                      30

Gly Met Ser Trp Val Arg Gln Ala Pro Gly Lys Gly Leu Glu Trp Val
        35                      40                      45

Ala Asn Ile Asn Thr Phe Gly Asp Arg Thr Tyr Tyr Val Asp Ser Val
    50                      55                      60

Lys Gly Arg Phe Thr Ile Ser Arg Asp Asn Ala Lys Asn Ser Leu Tyr
65              70                      75                      80

Leu Gln Met Asn Ser Leu Arg Ala Glu Asp Thr Ala Val Tyr Tyr Cys
                85                      90                      95

Ala Arg Gly Thr Gly Thr Tyr Trp Gly Gln Gly Thr Leu Val Thr Val
                100                     105                     110

Ser Ser

FIG. 3L hV$_L$ MAb13(a)

Asp Val Val Met Thr Gln Ser Pro Leu Ser Leu Pro Val Thr Leu Gly
1           5               10              15

Gln Pro Ala Ser Ile Ser Cys Arg Ser Ser Gln Ser Leu Leu Asp Ser
            20              25              30

Asp Gly Lys Thr Tyr Leu Asn Trp Phe Gln Gln Arg Pro Gly Gln Ser
          35            40              45

Pro Arg Arg Leu Ile Tyr Leu Val Ser Asn Arg Asp Ser Gly Val Pro
        50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Trp Gln Gly
            85              90              95

Thr His Phe Pro Gln Thr Phe Gly Gly Gly Thr Lys Val Glu Ile Lys
          100             105             110

FIG. 3M hV$_H$ MAb13(b)

Glu Val Gln Leu Val Glu Ser Gly Gly Gly Leu Val Gln Pro Gly Gly
1           5                   10                  15

Ser Leu Arg Leu Ser Cys Ala Ala Ser Gly Phe Ile Phe Ser Ser Tyr
            20              25                  30

Gly Met Ser Trp Val Arg Gln Ala Pro Gly Lys Gly Leu Glu Trp Val
            35              40                  45

Ala Ser Ile Asn Thr Phe Gly Asp Arg Thr Tyr Tyr Val Asp Ser Val
        50                  55              60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

FIG. 3N hV$_L$ MAb13(b)

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25              30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
                100                 105                 110
```

FIG. 3O hV$_H$ MAb16(a)

Gln Val Gln Leu Val Gln Ser Gly Ala Glu Val Lys Lys Pro Gly Ala
1              5                   10                  15

Ser Val Lys Val Ser Cys Lys Ala Ser Gly Tyr Thr Phe Thr Ser Tyr
              20                  25                  30

Tyr Met Tyr Trp Val Arg Gln Ala Pro Gly Gln Gly Leu Glu Trp Met
         35                  40                  45

Gly Ile Ile Asn Pro Ser Asn Gly Gly Thr Ser Tyr Ala Gln Lys Phe
     50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
               85                  90                  95

Thr Arg Gly Gly Tyr Tyr Pro Phe Asp Tyr Trp Gly Gln Gly Thr Thr
              100                 105                 110

Val Thr Val Ser Ser
         115

FIG. 3P hV<sub>L</sub> MAb16(a)

```
Asp Val Val Met Thr Gln Ser Pro Leu Ser Leu Pro Val Thr Leu Gly
1             5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110
```

FIG. 3Q hV$_H$ MAb16(b)

Gln Val Gln Leu Val Gln Ser Gly Ala Glu Val Lys Lys Pro Gly Ala
1           5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
        115

FIG. 3R hV$_L$ MAb16(b)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25              30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

FIG. 3S hV$_H$ MAb16(c)

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115
```

FIG. 3T hV$_L$ MAb16(c)

Asp Val Val Met Thr Gln Ser Pro Leu Ser Leu Pro Val Thr Leu Gly
1              5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                      95

Thr His Ser Pro Tyr Thr Phe Gly Gln Gly Thr Lys Leu Glu Ile Lys
            100                 105                 110

FIG. 3U hV_H MAb19(a)

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Asp
20 25 30

Tyr Ala Trp Asn Trp Ile Arg Gln His Pro Gly Lys Gly Leu Glu Trp
35 40 45

Ile Gly Tyr Ile Ser Phe Ser Gly Tyr Thr Tyr Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Glu Val Asn Tyr Gly Asp Ser Tyr His Phe Asp Tyr Trp Gly
100 105 110

Gln Gly Thr Leu Val Thr Val Ser Ser
115 120

FIG. 3V hV$_L$ MAb19(a)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
            35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

FIG. 3W hV$_H$ MAb19(b)

Gln Val Gln Leu Gln Glu Ser Gly Pro Gly Leu Val Lys Pro Ser Gln
1           5               10              15

Thr Leu Ser Leu Thr Cys Thr Val Ser Gly Tyr Ser Ile Thr Ser Asp
            20              25              30

Tyr Ala Trp Ser Trp Ile Arg Gln His Pro Gly Lys Gly Leu Glu Trp
            35              40              45

Ile Gly Tyr Ile Ser Phe Ser Gly Tyr Thr Tyr Tyr Asn Pro Ser Leu
            50              55              60

Lys Ser Arg Val Thr Ile Ser Val Asp Thr Ser Lys Asn Gln Phe Ser
65              70              75              80

Leu Lys Leu Ser Ser Val Thr Ala Ala Asp Thr Ala Val Tyr Tyr Cys
            85              90              95

Ala Arg Glu Val Asn Tyr Gly Asp Ser Tyr His Phe Asp Tyr Trp Gly
            100             105             110

Gln Gly Thr Leu Val Thr Val Ser Ser
            115             120

FIG. 3X hV$_L$ MAb19(b)

Gln Leu Val Leu Thr Gln Ser Pro Ser Ala Ser Ala Ser Leu Gly Ala
1           5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

FIG. 3Y hV<sub>H</sub> MAb19(c)

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120
```

FIG. 3Z hV$_L$ MAb19(c)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Gln Pro Glu Lys Gly Pro Arg Tyr Leu Met
                35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
                100                 105                 110

Glu Ile Lys
    115
```

PROPHYLAXIS OF COLORECTAL AND GASTROINTESTINAL CANCER

1. REFERENCE TO RELATED APPLICATIONS

This application claims the benefit under 35 U.S.C. § 119(e) of provisional application No. 61/317,245, filed Mar. 24, 2010, the content of which is incorporated by reference in its entirety.

2. REFERENCE TO SEQUENCE LISTING, TABLE OR COMPUTER PROGRAM

The Sequence Listing is concurrently submitted herewith.

3. FIELD OF THE INVENTION

The present disclosure is directed to, among other things, methods of preventing colorectal and/or gastrointestinal cancer in subjects predisposed to develop adenomatous polyps by administering to the subject a composition comprising an antibody specific for progastrin.

4. BACKGROUND

Cancer of the gastrointestinal tract, including colorectal cancer ("CRC"), affects hundreds of thousands of individuals every year and tens of thousands of CRC-related deaths occur every year in the United States alone. See, Rustgi, 2010, "The genetics of hereditary colon cancer," *Genes & Development* 21:2525-2538. CRC can arise in different ways, one of which is the transformation of adenomatous polyps into malignant tumors. Adenomatous polyposis may be inherited, as is the case for individuals with familial adenomatous polyposis ("FAP"), or it may be sporadic. Individuals with FAP or sporadic adenomatous polyposis carry mutations of the Adenomatous Polyposis Coli ("APC") tumor suppressor gene which are associated with the formation of adenomatous polyps in the small intestine, colon and/or rectum. These polyps in turn can develop into colorectal and gastrointestinal cancer. In the case of sporadic adenomatous polyposis, a non-hereditary condition that underlies many instances of CRC, the APC gene is mutated in somatic cells. Individuals with sporadic adenomatous polyposis develop benign polyps, a subset of which may subsequently transform into malignant carcinomas.

FAP accounts for around 1% of total CRC cases and affects one in 13,000 births. Id. Mutation of APC in FAP patients is associated with the formation of hundreds to thousands of small adenomatous polyps throughout the colon. Progression of polyps to malignancy is virtually inevitable. On average, without prophylactic treatment, individuals with FAP develop CRC by age 39. Prophylactic treatment is the standard of care and involves radical surgery, including the removal of the colon, or of both the colon and the rectum, generally before the age of 25. While prophylaxis is preferable to no treatment, surgical resection of the colon (colectomy) in young patients severely impairs quality of life. In addition, surgical resection alone may be inadequate to keep patients cancer-free: patients who have colectomies have a high risk of developing polyps and cancer in the upper gastrointestinal tract. There is a serious need for effective prophylactic treatments, especially non-surgical treatments, that extend cancer-free life for individuals with FAP and individuals with sporadic adenomatous polyposis.

5. SUMMARY

The present disclosure provides methods and compositions useful for preventing gastrointestinal cancer, including CRC, in animals, including humans, predisposed to developing adenomatous polyps. As described below, the present application sets forth treatment regimens believed to bind progastrin ("PG"), with the apparent ability to neutralize PG's biological activity, which are useful in subjects who have an increased likelihood of developing, but have not yet developed, CRC or cancer in the upper gastrointestinal tract. The various inventions described in the application are based in part on the applicants' discovery that anti-PG antibodies prevent the development of gastrointestinal tumors in a mouse model of FAP. While not intending to be bound by any theory of operation, binding PG and interfering with its interaction with other proteins in the body is thought to prevent adenomatous polyps from developing into malignant tumors.

Accordingly, in one aspect, the present disclosure provides methods of preventing gastrointestinal cancer, including CRC, in subjects predisposed to developing adenomatous polyps by administering a composition comprising an anti-PG antibody. Generally, the methods comprise administering to a subject in need thereof an effective amount of an anti-PG antibody. Anti-PG antibodies, and compositions thereof, can be administered according to regimens known in the art for antibody-based therapy, at an effective dosage, i.e., an amount effective to prevent or delay gastrointestinal cancer, including CRC, in a subject.

Suitable subjects for prophylactic anti-PG treatment are those predisposed to developing adenomatous polyps, including subjects with a family history of CRC, individuals with FAP, and those in whom adenomatous polyps have previously been found and/or removed. Typically, suitable subjects have one or more mutations in the APC gene, leading to FAP or sporadic adenomatous polyposis. Suitable subjects also include individuals who have previously had a colectomy and are at increased risk of developing polyps and cancer in the upper gastrointestinal tract.

Anti-PG antibodies of the present disclosure include antibodies capable of binding PG. Any antibody capable of binding PG may be used in the methods of the present disclosure, including, but not limited to, polyclonal and monoclonal anti-PG antibodies. Preferably, the anti-PG antibody is specific to the PG of the species being treated. For example, an anti-human PG (anti-hPG) antibody is administered to a human subject. Suitable anti-PG antibodies can range in binding affinity from at least about 5000 nM to at least about 0.001 nM, or higher, or any value in between.

Anti-PG antibodies described herein can be used in combination with, or adjunctive to, other treatments to prevent or delay gastrointestinal cancer, including CRC. Non-limiting examples of other treatments include surgical resection, chemotherapy, antibody therapy, radiation therapy, and treatment with a second agent as described herein. Anti-PG antibodies can be administered concurrently with, or at a time before or after, another treatment.

Compositions suitable for use in the methods of the present disclosure may comprise, in addition to an anti-PG antibody, a pharmaceutically acceptable carrier, excipient, and/or diluent. The compositions can be formulated for various routes of administration as described herein, comprising carriers, excipients, and/or diluents suitable for the chosen route. For treatment in humans and animals, compositions comprising anti-PG antibodies can be administered using any suitable route of administration, such as injection and other routes of administration known in the art for antibody-based clinical products. For treatment purposes, compositions can be packaged in unit doses for ease of use.

As shown herein, patients with multiple adenomatous polyps have elevated serum PG levels, whereas patients in whom polyps have been removed have low or undetectable serum PG levels. This discovery provides powerful new tools to diagnose and monitor the course of sporadic or familial adenomatous polyposis and its treatment.

Accordingly, in another aspect, the present disclosure provides methods of monitoring the efficacy of anti-PG treatment in an individual predisposed to developing adenomatous polyps. Generally, the methods comprise measuring a concentration, or level, of PG in a blood (serum, plasma, or whole blood) sample from the individual receiving anti-PG therapy, during or after a course of anti-PG therapy, and comparing the measured PG level to a baseline level of PG (e.g., a PG level in the individual at the start of treatment), wherein a measured PG level below that of the baseline level is indicative of treatment efficacy and a measured PG level above that of the baseline level is indicative of a lack of efficacy. In some embodiments, the method further includes assessing the number and sizes of polyps in the subject by, for example, endoscopy.

In yet another aspect, the present disclosure provides methods for selecting individuals, in whom endoscopy or anti-PG treatment is indicated. The methods are intended to be carried out in individuals predisposed to developing adenomatous polyps. Generally, the method is carried out by measuring the level of PG in a blood sample from the individual, and comparing the measured level of PG to a baseline level, where a measured PG level higher than the baseline level indicates a need for endoscopy. In some embodiments, a PG level above the baseline indicates a need for anti-PG treatment. The baseline can be obtained from one or more samples from the individual at an earlier point in time, or can be based upon PG levels measured in a population having characteristics similar to the individual.

6. BRIEF DESCRIPTION OF THE FIGURES

FIG. 1 provides amino acid sequences of human preprogastrin (SEQ ID NO:100), where the signal peptide sequence is underlined, mature human progastrin (SEQ ID NO:20) and certain products of progastrin processing, including G34 (SEQ ID NO:102), G34-Gly (SEQ ID NO:103), G17 (SEQ ID NO:104), G17-Gly (SEQ ID NO:105) and CTFP (SEQ ID NO:106).

FIGS. 2A-2L provide polynucleotide and amino acid sequences of variable light and variable heavy chains of certain exemplary murine anti-hPG monoclonal antibodies. In each case, the three CDRs are shown in bolded-underlined text. Specifically:

FIG. 2A provides the polypeptide sequence of the $V_H$ chain of murine anti-hPG MAb3 (SEQ ID NO:12) and a polynucleotide sequence encoding it (SEQ ID NO:16);

FIG. 2B provides the polypeptide sequence of the $V_L$ chain of murine anti-hPG MAb3 (SEQ ID NO:13) and a polynucleotide sequence encoding it (SEQ ID NO:17);

FIG. 2C provides the polypeptide sequence of the $V_H$ chain of murine anti-hPG MAb4 (SEQ ID NO:14) and a polynucleotide sequence encoding it (SEQ ID NO:18);

FIG. 2D provides the polypeptide sequence of the $V_L$ chain of murine anti-hPG MAb4 (SEQ ID NO:15) and a polynucleotide sequence encoding it (SEQ ID NO:19);

FIG. 2E provides the polypeptide sequence of the $V_H$ chain of murine anti-hPG MAb8 (SEQ ID NO:59) and a polynucleotide sequence encoding it (SEQ ID NO:67);

FIG. 2F provides the polypeptide sequence of the $V_L$ chain of murine anti-hPG MAb8 (SEQ ID NO:63) and a polynucleotide sequence encoding it (SEQ ID NO:71);

FIG. 2G provides the polypeptide sequence of the $V_H$ chain of murine anti-hPG MAb13 (SEQ ID NO:60) and a polynucleotide sequence encoding it (SEQ ID NO:68);

FIG. 2H provides the polypeptide sequence of the $V_L$ chain of murine anti-hPG MAb13 (SEQ ID NO:64) and a polynucleotide sequence encoding it (SEQ ID NO:72);

FIG. 2I provides the polypeptide sequence of the $V_H$ chain of murine anti-hPG MAb16 (SEQ ID NO:61) and a polynucleotide sequence encoding it (SEQ ID NO:69);

FIG. 2J provides the polypeptide sequence of the $V_L$ chain of murine anti-hPG MAb16 (SEQ ID NO:65) and a polynucleotide sequence encoding it (SEQ ID NO:73);

FIG. 2K provides the polypeptide sequence of the $V_H$ chain of murine anti-hPG MAb19 (SEQ ID NO:62) and a polynucleotide sequence encoding it (SEQ ID NO:70); and FIG. 2L provides the polypeptide sequence of the $V_L$ chain of murine anti-hPG MAb19 (SEQ ID NO:66) and a polynucleotide sequence encoding it (SEQ ID NO:74).

FIGS. 3A-3Z provide projected polypeptide sequences for humanized variable heavy and light chains of selected anti-hPG monoclonal antibodies described herein. In each case, the three CDRs are shown in bolded-underlined text. Specifically:

FIG. 3A provides the projected amino acid sequence of the $V_H$ chain of humanized MAb3 (SEQ ID NO:21);

FIG. 3B provides the projected amino acid sequence of the $V_L$ chain of humanized MAb3 (SEQ ID NO:22);

FIG. 3C provides the projected amino acid sequence of the $V_H$ chain of humanized MAb4 (SEQ ID NO:23);

FIG. 3D provides the projected amino acid sequence of the $V_L$ chain of humanized MAb4 (SEQ ID NO:24);

FIG. 3E provides the projected amino acid sequence of the $V_H$ chain of humanized MAb8(a) (SEQ ID NO:75);

FIG. 3F provides the projected amino acid sequence of the $V_L$ chain of humanized MAb8(a) (SEQ ID NO:76);

FIG. 3G provides the projected amino acid sequence of the $V_H$ chain of humanized MAb8(b) (SEQ ID NO:77);

FIG. 3H provides the projected amino acid sequence of the $V_L$ chain of humanized MAb8(b) (SEQ ID NO:78);

FIG. 3I provides the projected amino acid sequence of the $V_H$ chain of humanized MAb8(c) (SEQ ID NO:79);

FIG. 3J provides the projected amino acid sequence of the $V_L$ chain of humanized MAb8(c) (SEQ ID NO:76);

FIG. 3K provides the projected amino acid sequence of the $V_H$ chain of humanized MAb13(a) (SEQ ID NO:80);

FIG. 3L provides the projected amino acid sequence of the $V_L$ chain of humanized MAb13(a) (SEQ ID NO:81);

FIG. 3M provides the projected amino acid sequence of the $V_H$ chain of humanized MAb13(b) (SEQ ID NO:82);

FIG. 3N provides the projected amino acid sequence of the $V_L$ chain of humanized MAb13(b) (SEQ ID NO:83);

FIG. 3O provides the projected amino acid sequence of the $V_H$ chain of humanized MAb16(a) (SEQ ID NO:84);

FIG. 3P provides the projected amino acid sequence of the $V_L$ chain of humanized MAb 16(a) (SEQ ID NO:85);

FIG. 3Q provides the projected amino acid sequence of the $V_H$ chain of humanized MAb16(b) (SEQ ID NO:86);

FIG. 3R provides the projected amino acid sequence of the $V_L$ chain of humanized MAb16(b) (SEQ ID NO:87);

FIG. 3S provides the projected amino acid sequence of the $V_H$ chain of humanized MAb16(c) (SEQ ID NO:88);

FIG. 3T provides the projected amino acid sequence of the $V_L$ chain of humanized MAb16(c) (SEQ ID NO:89);

FIG. 3U provides the projected amino acid sequence of the $V_H$ chain of humanized MAb19(a) (SEQ ID NO:90);

FIG. 3V provides the projected amino acid sequence of the $V_L$ chain of humanized MAb19(a) (SEQ ID NO:91);

FIG. 3W provides the projected amino acid sequence of the $V_H$ chain of humanized MAb19(b) (SEQ ID NO:92);

FIG. 3X provides the projected amino acid sequence of the $V_L$ chain of humanized MAb19(b) (SEQ ID NO:93);

FIG. 3Y provides the projected amino acid sequence of the $V_H$ chain of humanized MAb19(c) (SEQ ID NO:94); and FIG. 3Z provides the projected amino acid sequence of the $V_L$ chain of humanized MAb19(c) (SEQ ID NO:95).

7. DETAILED DESCRIPTION

7.1 Cancer In Familial And Sporadic Adenomatous Polyposis

Familial Adenomatous Polyposis (FAP) is a rare hereditary condition associated with a germinal mutation on one allele of the APC gene. Numerous mutations of the APC gene have been mapped in subjects with FAP, many of the mutations resulting in a truncated protein. See, e.g., Rustgi, 2010, "The genetics of hereditary colon cancer," *Genes & Development* 21:2525-2538; Groves et al., 2002, "Duodenal cancer in patients with familial adenomatous polyposis (FAP): results of a 10 year prospective study," *Gut* 50:636-641. These mutations in APC are associated with FAP of varying severity.

FAP is characterized by the appearance of multiple adenomas (polyps) in the intestine and colon of affected individuals, at a very young age. A subset of these polyps transform into colorectal cancer (CRC), and FAP-derived CRC cases represent approximately 1% of total CRC cases. Where there is a family history of CRC, individuals typically undergo genetic testing at a very early age to detect the presence of a mutation in the APC gene. Classical follow-up in individuals found to have such mutations begins with colonoscopy, polyp resection where polyps are found, and if polyps are too numerous to remove endoscopically, partial or complete resection of the colon (colectomy). Most individuals with FAP will have undergone colectomy by the age of 25.

A large percentage of sporadic adenomatous polyps also harbor mutations in the APC gene. See, Rutsgi, 2010, "The genetics of hereditary colon cancer," *Genes & Development* 21:2525-2538. In the absence of any family history of CRC, individuals presenting with symptoms such as rectal bleeding are typically examined by colonoscopy. Individuals found to have large numbers of polyps, or in whom polyps recur after resection, will typically also be tested genetically. If a mutation in the APC gene is found, colectomy is the recommended treatment.

Even after colectomy, individuals predisposed to developing adenomatous polyps have an increased risk of developing adenomatous polyps in the unresected portion of their gastrointestinal tracts. Such individuals are regularly followed by endoscopy and assessed for adenomatosis in the upper gastrointestinal tract. Individuals are staged according to the Spigelman classification, which relies on four parameters to evaluate the degree or severity of adenomatosis: number of polyps, size of polyps, histology of polyps, and degree of polyp dysplasia (disordered growth). See, Spigelman et al., 1989, "Upper gastrointestinal cancer in patients with Familial Adenomatous Polyposis," *Lancet* 2:783-785. The Spigelman classification categorizes individuals into one of five stages for duodenal polyposis, Stage 0 to IV, based on the four parameters, as shown in Table 1:

TABLE 1

Spigelman Classification

| Points | Number of polyps | Polyp size (mm) | Histology | Dysplasia |
| --- | --- | --- | --- | --- |
| 1 | 1-4 | 1-4 | Tubular | Mild |
| 2 | 5-20 | 5-10 | Tubulovillous | Moderate |
| 3 | >20 | >10 | Villous | Severe |

Stage I: 1-4 points;
Stage II: 5-6 points;
Stage III: 7-8 points;
Stage IV: 9-12 points.

A ten-year study of 114 individuals with FAP revealed that Spigelman Stage IV patients had a 36.4% risk of developing duodenal cancer, as compared to a 0% to 2.4% risk for patients classified in Stages 0 to III. See, Groves et al., 2002, "Duodenal cancer in patients with familial adenomatous polyposis (FAP): results of a 10 year prospective study," *Gut* 50:636-641.

It has previously been shown that approximately 70% of patients with CRC have elevated levels of PG. As shown in the Examples below, Applicants have now discovered that blood levels of PG can be elevated in individuals with FAP who have not yet developed CRC, as well as in about 20% of patients exhibiting sporadic adenomatous polyposis. While not intending to be bound by any theory of operation, PG is thought to be part of the mechanism by which polyps transition to malignant tumors. Binding of PG by anti-PG antibodies is thought to interfere with this transition, as demonstrated in the mouse model of FAP, APCΔ14. Prophylactic treatment with anti-PG antibodies presents the possibility of avoiding or delaying major surgery, significantly increasing quality of life.

7.2 Methods of Prophylaxis

The present disclosure provides methods of preventing gastrointestinal cancer, including CRC, in patients predisposed to developing adenomatous polyps. Generally, the methods comprise administering to such patients an amount of one or more anti-PG antibody(ies) effective to provide a therapeutic benefit. Anti-PG antibodies generally, and specific anti-PG antibodies useful in the methods, are described in detail in a later section.

The "subject" or "patient" for prophylaxis is preferably a mammal such as a non-primate (e.g., cow, pig, horse, cat, dog, rat, etc.) or a primate (e.g., monkey or human). The anti-PG antibody administered should be specific for the species of animal being treated. For treatment of human subjects, the anti-PG antibody(ies) should specifically bind human progastrin (referred to herein as "anti-hPG antibodies," described in more detail below).

The subject or patient can be a human, such as an adult patient or a pediatric patient. Suitable subjects are individuals who are predisposed to developing adenomatous polyps and, as a result, have an increased likelihood of developing CRC or gastrointestinal cancer, including individuals with a family history of CRC, individuals in whom adenomatous polyps are or have been detected or removed, individuals with FAP, individuals who have had a colectomy to remove polyps, and individuals with mutation(s) in the APC gene.

Anti-PG treatment can be administered in combination with, or adjunctive to, one or more other treatments to prevent or delay gastrointestinal cancer, including CRC. Other treatments include, without limitation, chemotherapeutic treatment, radiation, surgical resection, antibody therapy, and treatment with a second agent, as described herein. Combination treatment as provided herein involves the administration of at least two treatments to a patient, the first of which is anti-PG treatment with at least one anti-PG antibody, and the second of which is treatment with a therapeutic or prophylactic agent or procedure.

Anti-PG treatment can be combined with surgical procedures, such as surgical resection. Anti-PG antibodies can be administered to subjects found to have, or predisposed to develop, pre-cancerous polyps, such as individuals with familial adenomatous polyposis, in combination with surgical resection of the affected portion(s) of the gastrointestinal tract. Anti-PG treatment can be initiated before, concurrently with, or after surgical resection.

Anti-PG treatment can also be combined with radiation therapy. Radiation therapy is the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy, or brachytherapy). Systemic radiation therapy uses a radioactive substance, such as a radiolabeled monoclonal antibody, that travels in the blood to tissues throughout the body. Radiation therapy may also be called irradiation and radiotherapy. Other radiation therapies include three-dimensional conformal radiation therapy (3D-CRT) and intensity modulated radiation therapy (IMIRT). Other radiation therapies are also possible.

Where anti-PG antibody treatment is combined with a second agent, the second agent can be a chemotherapeutic agent. Chemotherapy is the use of small molecule drugs that kill (cytotoxic or cytocidal) or prevent the growth (cytostatic) of cancer cells. Chemotherapeutic agents include, but are not limited to, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, $E. coli$ L-asparaginase, emetine, epoetin-α, $Erwinia$ L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, oxaliplatin, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, tegafur, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Anti-PG antibodies can also be administered with a combination of chemotherapeutic agents. Exemplary combinations of chemotherapeutic agents include 5-fluorouracil (5FU) in combination with leucovorin (folinic acid or LV); capecitabine, in combination with uracil (UFT) and leucovorin; tegafur in combination with uracil (UFT) and leucovorin; oxaliplatin in combination with 5FU, or in combination with capecitabine; irinotecan in combination with capecitabine, mitomycin C in combination with 5FU, irinotecan or capecitabine. Other combinations of chemotherapeutic agents disclosed herein is also possible.

Standard dosing regimens for chemotherapeutic agents used for patients suffering from CRC may be used in the methods of the present disclosure. As is known in the relevant art, chemotherapy regimes for colorectal cancer using combinations of different chemotherapeutic agents have been standardized in clinical trials. Such regimes are often known by acronyms and include 5FU Mayo, 5FU Roswell Park, LVFU2, FOLFOX, FOLFOX4, FOLFOX6, bFOL, FUFOX, FOLFIRI, IFL, XELOX, CAPDX, XELIRI, CAPIRI, FOLFOXIRI. See, e.g., Chau, I. et al., 2009, $Br. I, Cancer$ 100:1704-19, and Field, K. et al., 2007, $Worlds. Gastroenterol.$ 13:3806-15, both of which are incorporated by reference.

Anti-PG antibodies can also be used in combination with other antibodies, including but not limited to, monoclonal antibodies that directly or indirectly kill, slow or stop the growth of cancer cells. Such antibodies can function through a variety of distinct mechanisms. For example, certain antibodies can mark cancer cells for attack by the patient's immune system via antibody-dependent cell-mediated cytotoxicity (ADCC) or other mechanisms. It is believed that rituximab (Rituxan®), which binds the CD20 antigen found on B cells, and edrecolomab, which binds the 17-1A antigen, function this way. Other antibodies bind to and alter or inhibit the function of antigens that cancer cells require for survival and/or growth. A number of antibodies are believed to function this way, including, for example, cetuximab (Erbitux®) and panitumumab (Vectibix®), each of which binds to the EGF receptor (EGFR); and bevacizumab (Avastin®), which binds to the growth factor VEGF. Other mechanisms are also possible, and particular antibodies may be able to work via one or more mechanisms of action. Yet other antibodies can be conjugated to radioactive or chemotoxic moieties and target them to cancer cells which preferentially express antigens specifically recognized by the antibodies.

Anti-PG antibodies can also be administered in combination with non-steroidal anti-inflammatory drugs ("NSAIDs"). For example, celecoxib, or 4-[5-(4-methylphenyl)-3-(trifluoromethyl) pyrazol-1-yl]benzenesulfonamie, is an NSAID that has been shown to reduce adenomatous polyps in FAP patients.

The anti-PG antibody and a second agent can be administered simultaneously, successively, or separately. As used herein, the anti-PG antibody and the second agent are said to be administered successively if they are administered to the patient on the same day, for example during the same patient visit. Successive administration can occur 1, 2, 3, 4, 5, 6, 7 or 8 hours apart. In contrast, the anti-PG antibody and the second agent are said to be administered separately if they are administered to the patient on different days, for example, the anti-PG antibody and the second therapeutic agent can be administered at a 1-day, 2-day or 3-day, one-week, 2-week or monthly intervals. In the methods of the present disclosure, administration of the anti-PG antibody of the disclosure can precede or follow administration of the second agent.

As a non-limiting example, the anti-PG antibody and second agent can be administered concurrently for a period of time, followed by a second period of time in which the administration of anti-PG antibody and the second agent are alternated.

7.3 Pharmaceutical Compositions And Kits

Anti-PG antibodies useful in the methods of the present disclosure can be formulated in compositions. Optionally, the compositions can comprise one or more additional agent(s), such as the second agents described above. The compositions will usually be supplied as part of a sterile, pharmaceutical composition that will normally include a pharmaceutically acceptable carrier. This composition can be in any suitable form (depending upon the desired method of administering it to an individual).

Anti-PG antibodies can be administered to an individual by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject. Antibodies can be formulated as an aqueous solution and administered by subcutaneous injection. Pharmaceutically acceptable carriers for use in the disclosure can take a wide variety of forms depending, e.g., on the condition to be treated or route of administration.

Pharmaceutical compositions can be conveniently presented in unit dose forms containing a predetermined amount of an anti-PG antibody per dose. Such a unit can contain for example 5 mg to 5 g, for example 10 mg to 1 g, or 20 to 50 mg of anti-PG antibody per unit dose. Pharmaceutical compositions can comprise anti-PG antibodies capable of binding more than one PG epitope. Alternatively, pharmaceutical compositions may comprise a combination of anti-PG antibodies, each capable of binding a different PG epitope.

Pharmaceutical compositions of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, e.g., *Remington's Pharmaceutical Sciences*, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

Anti-PG antibodies can be administered singly, as mixtures of one or more anti-PG antibodies, in mixture or combination with other agents useful in preventing CRC, or adjunctive to therapy for CRC. Examples of suitable combination and adjunctive therapies are provided above.

Encompassed by the present disclosure are pharmaceutical kits containing the anti-PG antibodies (including antibody conjugates) of the disclosure. The pharmaceutical kit is a package comprising the anti-PG antibody composition (e.g., either in lyophilized form or as an aqueous solution) and one or more of the following:

A second agent, for example as described above;
A device for administering an anti-PG antibody composition, for example a pen, needle and/or syringe; and
Pharmaceutical grade water or buffer to re-suspend the antibody if the antibody is in lyophilized form.

Each unit dose of anti-PG antibody can be packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

7.4 Effective Dosages And Treatment Regimens

The anti-PG antibodies of the present disclosure are administered to the subject in an amount sufficient or effective to provide a therapeutic benefit. In the context of preventing gastrointestinal cancer, including CRC, in a subject predisposed to develop adenomatous polyps, a therapeutic benefit can be inferred if one or more of the following is achieved: reduction or lack of increase in the number and/or size of polyps in a subject; absence of malignant tumors, including where a subject has or had polyps; reduction or lack of increase in plasma or serum PG level; regression from a more advanced stage of polyposis to a less advanced stage of polyposis, according to Spigelman's classification (e.g., regression from Stage IV to Stage III, from Stage III to Stage II, from Stage II to Stage I); lack of progression from Spigelman Stage IV polyposis to gastrointestinal cancer. Pharmaceutical compositions comprising anti-PG antibodies can be administered to individuals (e.g., human subjects) at effective dosages.

Complete prevention of gastronintestinal cancer, while desirable, is not required for therapeutic benefit to exist. Indeed, as most patients suffering from FAP require major surgery by the age of 25, slowing the progression of the disease such that surgery can be delayed improves quality of life. Furthermore, any delay in the onset of gastrointestinal cancer, such as CRC, provides a therapeutic benefit.

In some contexts, therapeutic benefit can be correlated with one or more surrogate end points, in accordance with the knowledge of one of ordinary skill in the art. By way of example and not limitation, plasma and/or serum PG concentrations can be measured in a subject over time, with a reduction in PG levels, or a level below a threshold level, for example, below about 50 pM, 40 pM, 30 pM, 20 pM, 10 pM, or 5 pM, being indicative of therapeutic benefit.

Polyp size and number can be measured using endoscopic techniques, such as colonoscopy, as well as other methods known to those of ordinary skill in the art.

Binding all free PG is not required to achieve therapeutic efficacy, although it may be desirable. Free PG means PG that is available to be bound by an anti-PG antibody. Rather, reducing the concentration of free PG within or around polyps, systemically, in particular body fluids, or elsewhere, to a more limited extent may also be effective. Exemplary tissues and body fluids in which free PG concentration may be reduced by administration of anti-PG antibody(ies) compositions include, but are not limited to, polyp or tumor samples removed from a patient, ascites fluid, fluid from pleural effusions, cerebrospinal fluid, lymph, blood, plasma, serum and others. The concentration of PG in one or more of these tissues or body fluids can be quantified using an ELISA technique or other techniques familiar to those of ordinary skill in the art.

In accordance with the knowledge of those ordinarily skilled in the art, the dose of an anti-PG antibody can be titrated in a patient so as to reduce the free PG concentration in a tissue or body fluid of interest at a predetermined time after administration at least about 10%, 20%, 30%, 40%, 50%, 60%, 70%, 80%, 90, or 100%, or about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-95%, or a percentage reduction in free PG concentration ranging between any of the foregoing values.

The amount of anti-PG antibody administered will depend on a variety of factors, including the number and size of adenomatous polyps found in the subject, the form, route and site of administration, the treatment regimen (e.g., whether a second therapeutic agent is used), the age and condition of the particular subject being treated, the sensitivity of the patient to anti-PG antibodies. The appropriate dosage can be readily determined by a person skilled in the art. Ultimately, a physician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of treatment using conventional techniques known to the people skilled of the art.

Effective dosages can be estimated initially from in vitro assays. For example, an initial dose for use in animals may be formulated to achieve a circulating blood or serum concentration of anti-PG antibody that is at or above the binding affinity of the antibody for progastrin as measured in vitro. Calculating dosages to achieve such circulating blood or serum concentrations taking into account the bioavailability of the particular antibody is well within the capabilities of skilled artisans. For guidance, the reader is referred to Fingl & Woodbury, "General Principles" in *Goodman and Gilman's The Pharmaceutical Basis of Therapeutics*, Chapter 1, latest edition, Pagamonon Press, and the references cited therein.

Initial dosages can be estimated from in vivo data, such as animal models. Animal models useful for testing the efficacy of compounds to delay or prevent development of gastrointestinal tumors, including CRC tumors, are well known in the art. Additionally, an animal model of FAP is described in the Examples below. Ordinarily skilled artisans can routinely adapt such information to determine dosages suitable for human administration.

In specific embodiments, an i.v. dose may be determined for an individual subject by measuring the serum or plasma PG concentration of the individual a few times a few days to a few weeks prior to treatment and calculating an amount of anti-PG antibody that would be saturating, i.e., an amount that would be sufficient to bind all of the PG. As will be appreciated by skilled artisans, the amount of any specific antibody necessary to achieve saturation for a given serum or plasma concentration of PG will depend, in part, on the affinity constant of the particular antibody. Methods for calculating saturating quantities for specific anti-PG antibodies of interest are well-known.

To insure saturation, an amount that is greater than the calculated saturating amount may be administered, for example, at least 2-, 3-, 4-, 5-, 6-, 7-, 8-, 9- or even 10-fold greater than the calculated saturating amount may be administered. For modes of administration other than i.v., the amount can be adjusted based upon pharmacokinetic and bioavailability, as is well known in the art.

The effective dose of an anti-PG antibody of the disclosure can range from about 0.001 to about 75 mg/kg per single (e.g. bolus) administration, multiple administrations or continuous (e.g. infusion) administration, or to achieve a serum concentration of 0.01-5000 μg/ml serum concentration per single administration, multiple administrations or continuous administration, or any effective range or value therein depending on the condition being treated, the route of administration and the age, weight and condition of the subject. In certain embodiments, each dose can range from about 0.1 mg/kg to about 0.5 mg/kg; about 0.25 mg/kg to about 0.75 mg/kg; about 0.5 mg/kg to about 1 mg/kg; about 1 mg/kg to about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg. Other dosage ranges are also possible.

Amount, frequency, and duration of administration will depend on a variety of factors, such as the patient's age, weight, and disease condition. Anti-PG treatment is indicated in subjects in whom pre-cancerous adenomatous polyps are detected and/or removed, and subjects diagnosed with FAP who have yet to manifest polyps. In humans with FAP, polyps generally begin to appear in the second decade. Anti-PG treatment can be initiated before or at the time polyps are detected in subjects with FAP. For subjects with sporadic adenomatous polyposis, anti-PG treatment can be initiated at the time polyps are detected. Anti-PG treatment can also be initiated in subjects who have had at least one polyp removed, and therefore are at increased risk of developing more polyps and gastrointestinal cancer, including CRC.

A treatment regimen for administration can continue for 2 weeks to indefinitely. Optionally, the treatment regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. An effective amount of anti-PG antibody can be administered as a single dose or over the course of a treatment regimen. The duration of anti-PG treatment for patients predisposed to develop adenomatous polyposis is preferably long, e.g., over the course of years, but may be shorter, e.g., one to several months, to a year.

7.5 Methods of Selecting Patients for Follow-Up or Treatment, and Patient Monitoring to Determine Treatment Efficacy Without wishing to be bound by any particular theory of operation, it is believed that elevated levels of PG are associated with the transformation of adenomatous polyps from benign to malignant. As shown in Example 6 below, subjects with multiple polyps had elevated PG levels whereas subjects who did not have polyps had either low or undetectable levels of serum PG. Based on this observation, plasma and/or serum levels of PG can be used to identify patients for follow-up or treatment, as well as to monitor the effectiveness of prophylaxis in patients undergoing treatment.

Monitoring PG levels in individuals with FAP or a history of sporadic adenomatous polyposis is useful for identifying subjects in whom follow up by colonoscopy is warranted, as well as patients in need of anti-PG treatment. Standard care for individuals predisposed to developing adenomatous polyps is endoscopy at an interval of 3 to 5 years. This interval between testing may mean that, in certain individuals, numerous polyps have developed or cancer has set in by the time follow up endoscopy is performed. A simple blood test for PG levels is readily performed at more frequent intervals and can identify those individuals who should undergo endoscopy (e.g., colonoscopy) sooner or who are candidates for anti-PG treatment.

An individual diagnosed with FAP or in whom polyps have previously been detected can be monitored to determine PG level, or concentration, in a bodily fluid, such as whole blood, plasma, or serum, relative to an appropriate baseline. Accordingly, a PG level is measured in a sample from the individual and then compared to a baseline PG level.

Where the PG level in a subject with FAP or a history of sporadic adenomatous polyposis is unchanged relative to previous measurements in the subject or equal to a baseline level for the relevant population to which the subject is being compared, the subject is scored as not requiring further follow up. By contrast, where the PG concentration is above the baseline, or is seen to rise over a period of time in the subject, the subject is a candidate for further follow-up, including, for example, colonoscopy, and for anti-PG treatment.

For purposes of monitoring efficacy of the treatment, blood, plasma, or serum PG levels can be measured in the patient receiving anti-PG treatment at specified time points, and used as an indication of whether the treatment is effective based on whether the measured level is above or below a baseline PG level. This information can be used by care providers to decide whether to continue administering an anti-PG antibody or modify treatment. These methods can be used to monitor anti-PG treatment, used alone, or in combination with other treatments, as described above.

In some embodiments of the methods, the PG level in one or more bodily fluids, such as whole blood, plasma, serum, of a patient receiving anti-PG antibody treatment can be measured and then compared to a baseline level. A decrease in concentration over time, and/or a measured level below a threshold value at a particular point in time, is indicative of efficacy. An increase in concentration over time and/or above-baseline PG level is indicative of lack of treatment efficacy. Typically, PG level is the concentration of PG in the sample, expressed in molar (M) amounts or moles/liter (mol/liter).

The baseline level can be a single number or a range of numbers. The baseline can be based on one or more measurements taken from the patient or based on measurements of PG in samples from a population of individuals. In some embodiments of the methods, the baseline is a PG level from the same patient, taken at one or more interval, for example, before the initiation of anti-PG treatment, during the course of treatment, or after treatment has been stopped. In some embodiments, the baseline can be an average PG level in a population of individuals with characteristics similar to those of the individual undergoing monitoring. Such characteristics may include, but are not necessarily limited to sex, age, location of mutation in APC gene, stage in Spigelman classification, history of surgery, anti-PG treatment, or other treatment. In some embodiments, the baseline is a specific PG level, such as about 50 pM, about 40 pM, about 30 pM, about 20 pM, about 10 pM, about 5 pM, about 2 pM, about 1 pM, or even lower. In some embodiments, the baseline is a range.

PG levels can be measured using techniques familiar to those of ordinary skill in the art, such as, but not limited to, RIA and ELISA. In a specific embodiment, PG levels may be measured using a sandwich ELISA with one anti-PG antibody targeting the N-terminus of progastrin and a second anti-PG antibody targeting the C-terminus of progastrin. Exemplary N- and C-terminal anti-PG antibodies useful for such a sandwich assay are described in a later section. In such an assay, a surface, such as the wells in a 96-well plate, is prepared to which a known quantity of a first, "capture," N-terminal or C-terminal anti-PG antibody is bound. A test sample is then applied to the surface followed by an incubation period. The surface is then washed and a solution containing a second, "detection," anti-PG antibody is applied, where the detection antibody binds a different epitope of PG (for example, if the capture antibody is a C-terminal anti-PG antibody, an N-terminal anti-PG antibody is used as the detection antibody, and vice versa). PG levels are then measured either directly (if, for example, the detection antibody is conjugated to a detectable label) or indirectly (through a labeled secondary antibody that binds the detection anti-PG antibody). For this assay, antibodies should be used in excess such that all PG is bound and quantified. A specific sandwich assay for measuring plasma and/or serum PG levels is provided in Example 1.

Multiple measurements at different intervals may be taken, and then graphed to determine if a trend exists. In a non-limiting example, PG levels can be determined at weekly, monthly, or annual intervals while a patient is received anti-PG antibodies. Other intervals are also possible.

In an embodiment involving a round of therapy using an anti-PG antibody, one or more measurements may also be taken during the course of therapy so that the effect of the antibodies on PG levels can be estimated. In other such embodiments, where residual anti-PG antibodies are present in a patient during sampling, the data may show a reduction in PG levels, due to sequestration of PG by the antibodies, followed by a rise, as this effect abates, followed by a subsequent decline, if the treatment was effective. In yet other embodiments, post-therapy measurements can be taken after it is estimated that the anti-PG antibodies have been cleared from the patient so that binding of PG by such antibodies does not affect the accuracy of the measurement of PG concentration.

Because eating usually increases gastrin synthesis and secretion, it may also cause transient increases in blood PG levels, which may interfere with the accurate measurement of PG levels in patients being monitored. To avoid this effect, particularly where PG concentration in blood samples is to be determined, samples can be taken from the patient after fasting.

7.6 Anti-PG Antibodies

Antibodies useful in the methods disclosed herein are those that specifically bind progastrin over other products of the gastrin gene. Referring to FIG. 1, the human gastrin gene is translated into a 101-amino acid polypeptide, called pre-progastrin, which contains a signal sequence (underlined) that is cleaved, giving rise to human progastrin, an 80-amino-acid polypeptide. Progastrin, in turn, is cleaved to generate a 34-amino-acid product, corresponding in sequence to residues 38-71 of progastrin, which is then extended at its carboxy terminus with a glycine residue, generating glycine-extended G34 ("G34-Gly"). A by-product of this cleavage is a 6-amino-acid peptide, called the C-terminal flanking peptide, or CTFP, which corresponds in sequence to residues 75-80 of progastrin. G34-Gly is then further cleaved to generate a 17-residue polypeptide corresponding in sequence to residues 55-71 of progastrin and referred to as G17-Gly. Removal of the C-terminal glycines of G34-Gly and G17-Gly, followed by C-terminal amidation, yields G34 and G17, respectively, both of which are C-terminal amidated.

As used herein, an antibody is "highly specific for" hPG or "highly specifically binds" hPG if it binds to full-length progastrin but does not bind at all to CTFP, to amidated gastrin, or to glycine-extended gastrin, and is "specific for" hPG or "specifically binds" hPG if it exhibits at least about 5-fold greater binding of hPG than CTFP and the other products of the gastrin gene, as measured in standard binding assays. A specific ELISA assay that can be used to assess the specificity of a particular anti-hPG antibody is provided in Example 2.

Such highly specific and/or specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The epitope bound by the anti-hPG antibodies is not critical. Useful anti-hPG antibodies may bind an N-terminal region of hPG, a C-terminal region of hPG, or a different region of hPG. Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076454 to Singh) and a peptide corresponding to the last ten amino acids at the C-terminal end of hPG (see WO 07/135542 to Hollande et al.) failed to generate monoclonal antibodies. As noted in the '329 and '041 applications, antigenic N-terminal and C-terminal sequences within the hPG sequence have been identified that can be used to generate nonoclonal antibodies that specifically bind hPG. Interestingly, the antigenic sequence need not be limited to regions of the hPG sequence that are unique to it. Peptide antigens having regions of sequence in common with other products of the gastrin gene, for example, G17, G34 and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDAPLG (SEQ ID NO:25). Exemplary immonogens useful for obtaining N-terminal anti-hPG antibodies, as well as CDR and $V_H$ and $V_L$ sequences of N-terminal anti-hPG monoclonal antibodies obtained with these exemplary immunogens, are provided in TABLE 2A, below, and the Example sections:

TABLE 2A

N-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| N1 | 43B9G11 | MAb1 | | | | |
| N1 | WE5H2G7 | MAb2 | | | | |
| N2 | 6B5B11C10 | MAb3 | $V_H$ CDR 1.3 | GYIFTSYW (SEQ ID NO: 1) | m$V_H$.3 (SEQ ID NO: 12) | h$V_H$.3 (SEQ ID NO: 21) |
| | | | $V_H$ CDR 2.3 | FYPGNSDS (SEQ ID NO: 2) | | |
| | | | $V_H$ CDR 3.3 | TRRDSPQY (SEQ ID NO: 3) | | |
| | | | $V_L$ CDR 1.3 | QSIVHSNGNTY (SEQ ID NO: 4) | m$V_L$.3 (SEQ ID NO: 13) | h$V_L$.3 (SEQ ID NO: 22) |
| | | | $V_L$ CDR 2.3 | KVS (SEQ ID NO: 5) | | |
| | | | $V_L$ CDR 3.3 | FQGSHVPFT (SEQ ID NO: 6) | | |
| N2 | 20D2C3G2 | MAb4 | $V_H$ CDR 1.4 | GYTFSSSW (SEQ ID NO: 7) | m$V_H$.4 (SEQ ID NO: 14) | h$V_H$.4 (SEQ ID NO: 23) |
| | | | $V_H$ CDR 2.4 | FLPGSGST (SEQ ID NO: 8) | | |
| | | | $V_H$ CDR 3.4 | ATDGNYDWFPAY (SEQ ID NO: 9) | | |
| | | | $V_L$ CDR 1.4 | QSLVHSSGVTY (SEQ ID NO: 10) | m$V_L$.4 (SEQ ID NO: 15) | h$V_L$.4 (SEQ ID NO: 24) |
| | | | $V_L$ CDR 2.4 | KVS (SEQ ID NO: 5) | | |
| | | | $V_L$ CDR 3.4 | SQSTHVPPT (SEQ ID NO: 11) | | |
| N2 | 1B9A4A4 (1-4376) | MAb15 | | | | |
| N2 | 1E9D9B6 | MAb16 | $V_H$ CDR 1.16 | GYTFTSYY (SEQ ID NO: 39) | mVH.16 (SEQ ID NO: 61) | h$V_H$.16a (SEQ ID NO: 84) |
| | | | $V_H$ CDR 2.16 | INPSNGGT (SEQ ID NO: 43) | hVH.16b (SEQ ID NO: 86) | |
| | | | $V_H$ CDR 3.16 | TRGGYYPFDY (SEQ ID NO: 47) | hVH.16c (SEQ ID NO: 88) | |
| | | | $V_L$ CDR 1.16 | QSLLDSDGKTY (SEQ ID NO: 50) | m$V_L$.16 (SEQ ID NO: 65) | h$V_L$.16a (SEQ ID NO: 85) |
| | | | $V_L$ CDR 2.16 | LVS (SEQ ID NO: 53) | h$V_L$.16b (SEQ ID NO: 87) | |
| | | | $V_L$ CDR 3.16 | WQGTHSPYT (SEQ ID NO: 57) | h$V_L$.16c (SEQ ID NO: 89) | |
| N2 | 1C8D10F5 | MAb17 | | | | |
| N2 | 1A7C3F11 | MAb18 | | | | |
| N2 | 1B3B4F11 | MAb19 | $V_H$ CDR 1.19 | GYSITSDYA (SEQ ID NO: 40) | m$V_H$.19 (SEQ ID NO: 62) | h$V_H$.19a (SEQ ID NO: 90) |
| | | | $V_H$ CDR 2.19 | ISFSGYT (SEQ ID NO: 44) | | h$V_H$.19b (SEQ ID NO: 92) |
| | | | $V_H$ CDR 3.19 | AREVNYGDSYHFDY (SEQ ID NO: 48) | | h$V_H$.19c (SEQ ID NO: 94) |
| | | | $V_L$ CDR 1.19 | SQHRTYT (SEQ ID NO: 51) | m$V_L$.19 (SEQ ID NO: 66) | h$V_L$.19a (SEQ ID NO: 91) |
| | | | $V_L$ CDR 2.19 | VKKDGSH (SEQ ID NO: 54) | | h$V_L$.19b (SEQ ID NO: 93) |
| | | | $V_L$ CDR 3.19 | GVGDAIKGQSVFV (SEQ ID NO: 58) | | h$V_L$.19c (SEQ ID NO: 95) |
| N2 | 1C11F5E8 | MAb20 | | | | |

Immunogen N1 = SWKPRSQQPDAPLG-Ahx-Cys-BSA, also represented as (SEQ ID NO: 25)-Ahx-Cys-B SA
Immunogen N2 = SWKPRSQQPDAPLG-Ahx-Cys-KLH, also represented as (SEQ ID NO: 25)-Ahx-Cys-KLH In TABLE 2A, all amino acid sequences are represented using conventional N→C orientation. For each immunogen, the progastrin peptide was synthesized with a C-terminal linker of one aminohexanoic acid (Ahx) residue followed by a cysteine (Cys) residue, which was then conjugated to a either a bovine serum albumin ("BSA") or keyhole limpet hemocyanin ("KLH") carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYG-WMDFGRRSAEDEN (SEQ ID NO:27). Exemplary immunogens including this antigen useful for obtaining C-terminal anti-hPG antibodies, as well as CDR and $V_H$ and $V_L$ sequences of C-terminal anti-hPG monoclonal antibodies obtained with these exemplary immunogens, are provided in TABLE 2B, below, and the Examples section.

TABLE 2B

C-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| C1 | 1B4A11D11 (I-4371) | MAb5 | | | | |
| C1 | 1B6A11F2 (I-4372) | MAb6 | | | | |
| C1 | 1B11E4B11 (I-4373) | MAb7 | | | | |
| C1 | 1C10D3B9 | MAb8 | $V_H$ CDR 1.8<br>$V_H$ CDR 2.8<br>$V_H$ CDR 3.8<br>$V_L$ CDR 1.8<br>$V_L$ CDR 2.8<br>$V_L$ CDR 3.8 | GFTFTTYA (SEQ ID NO: 37)<br>ISSGGTYT (SEQ ID NO: 41)<br>ATQGNYSLDF (SEQ ID NO: 45)<br>KSLRHTKGITF (SEQ ID NO: 49)<br>QMS (SEQ ID NO: 52)<br>AQNLELPLT (SEQ ID NO: 55) | m$V_H$.8 (SEQ ID NO: 59)<br><br>m$V_L$.8 (SEQ ID NO:63) | h$V_H$.8a (SEQ ID NO: 75)<br>h$V_H$.8b (SEQ ID NO: 77)<br>h$V_H$.8c (SEQ ID NO: 79)<br>h$V_L$.8a (SEQ ID NO: 76)<br>h$V_L$.8b (SEQ ID NO: 78)<br>h$V_L$.8c (SEQ ID NO: 76) |
| C1 | 1D8F5B3 | MAb9 | | | | |
| C1 | 1E1C7B4 | MAb10 | | | | |
| C1 | 2B4C8C8 (I-4374) | MAb11 | | | | |
| C1 | 2B11E6G4 (I-4375) | MAb12 | | | | |
| C1 | 2C6C3C7 | MAb13 | $V_H$ CDR 1.13<br>$V_H$ CDR 2.13<br>$V_H$ CDR 3.13<br>$V_L$ CDR 1.13<br>$V_L$ CDR 2.13<br>$V_L$ CDR 3.13 | GFIFSSYG (SEQ ID NO: 38)<br>INTFGDRT (SEQ ID NO: 42)<br>ARGTGTY (SEQ ID NO: 46)<br>QSLLDSDGKTY (SEQ ID NO: 50)<br>LVS (SEQ ID NO: 53)<br>WQGTHFPQT (SEQ ID NO: 56) | m$V_H$.13 (SEQ ID NO: 60)<br><br>m$V_L$.13 (SEQ ID NO: 64) | h$V_H$.13a (SEQ ID NO: 80)<br>h$V_H$.13b (SEQ ID NO: 82)<br>h$V_L$.13a (SEQ ID NO: 81)<br>h$V_L$.13b (SEQ ID NO: 83) |
| C1 | 2H9F4B7 | MAb14 | | | | |
| C2 | 1F11F5E10 | MAb21 | | | | |
| C2 | 1F11F5G9 | MAb22 | | | | |
| C2 | 1A11F2C9 | MAb23 | | | | |

Immunogen C1 = KLH-Cys-Ahx-QGPWLEEEEEAYGWMDFGRRSAEDEN, also represented as KLH-Cys-Ahx-Ahx- (SEQ ID NO: 27)
Immunogen C2 = DT-Cys-Ahx-QGPWLEEEEEAYGWMDFGRRSAEDEN, as also represented DT-Cys-Ahx-Ahx- (SEQ ID NO: 27)

In TABLE 2B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in TABLES 2A and 2B were mapped using the SPOT technique and alanine scanning, as described in Laune et al., 2002, J. Immunol. Methods 267:53-70 and Laune, 1997, J. Biol. Chem. 272:30937-30944, respectively (see also, Example 6 of the '329 application).

In the SPOT technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in TABLE 3A below.

TABLE 3A

| MAb# | PG peptide antigen: SWKPRSQQPDAPLG | SEQ ID NO |
|---|---|---|
| MAb2 | WKPRSQQPDAPLG | 32 |
| MAb4 | WKPRSQQPDAPLG | 32 |
| MAb1 | PDAPLG | 29 |
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbs5-7, 9-12, 14 and 21-23, epitopes comprise at least the following sequences: FGRR (SEQ ID NO:33), MDFGR (SEQ ID NO:34), AEDEN (SEQ ID NO:35), and GWMDFGRR (SEQ ID NO:36), as shown in TABLE 3B, below.

TABLE 3B

| MAb# | PG peptide antigen: QGPWLEEEEAYGWMDFGRRSAEDEN | SEQ ID NO |
|---|---|---|
| MAb14 | GWMDFGRR | 36 |
| MAb11 | MDFGR | 34 |
| MAb5 | FGRR | 33 |
| MAb6 | FGRR | 33 |

TABLE 3B-continued

| MAb# | PG peptide antigen: QGPWLEEEEAYGWMDFGRRSAEDEN | SEQ ID NO |
|---|---|---|
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in TABLES 2A & 2B can be identified in competitive binding assays with exemplary MAbs 1-23, or with other reference antibodies that bind N- or C-terminal epitopes, as will be described in more detail in a later section.

As also reported in the '329 and '041 applications, not all anti-hPG antibodies, even those that exhibit a high degree of specificity and affinity for hPG, may neutralize the biological activity of hPG. For example, although anti-hPG MAb14 binds hPG with a $K_D$ of about 6 pM, it did not inhibit the growth of colorectal cancer cells in an in vitro assay, whereas other anti-hPG monoclonal antibodies exhibited significant inhibitory activity (see, e.g., Example 7 of the '329 application). While both non-neutralizing and neutralizing antibodies that specifically bind hPG are useful for the various diagnostic and monitoring methods described herein, anti-hPG antibodies useful for therapeutic methods should exhibit neutralizing activity.

As used herein, a "neutralizing anti-hPG antibody" is an anti-hPG antibody that yields a statistically significant reduction in the number of live LS174T in a test sample treated with the anti-hPG antibody as compared to a control sample treated with a non-specific antibody. A specific assay for assessing the ability of any particular anti-hPG antibody to neutralize hPG is described in Example 3. Those anti-hPG antibodies that exhibit at least about a 50% reduction in the number of live cells in this assay are believed to be especially useful in methods of preventing gastrointestinal cancer, including CRC, although anti-hPG antibodies exhibiting lower levels of neutralizing activity, for example, a statistically significant reduction of 40%, 30%, 20%, 15%, or even 10%, in the number of live cells in this assay, are expected to provide therapeutic benefits.

Accordingly, in some embodiments, for example therapeutic embodiments, useful anti-hPG antibodies are neutralizing. As disclosed in the '329 and '041 applications, the ability of an anti-hPG monoclonal antibody is not epitope-dependent, as both N-terminal and C-terminal anti-hPG monoclonal antibodies exhibited neutralizing activity in assays with colorectal cancer cellsbearing a mutation in the APC gene. Thus, in some specific embodiments, the neutralizing anti-hPG antibodies are N-terminal neutralizing anti-hPG antibodies. In other embodiments, the neutralizing anti-hPG antibodies are C-terminal neutralizing anti-hPG antibodies.

The affinity of any specific anti-hPG antibody is not critical. However, for some uses, antibodies exhibiting affinities of at least about 1 μM may be preferred. For therapeutic uses, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, or even greater, may be desirable. The measured affinities of the anti-hPG monoclonal antibodies identified in TABLES 2A & 2B range from $10^{-6}$ to $10^{-12}$ M, as noted in TABLE 4, below:

TABLE 4

| MAb# | Affinity (measured $K_D$) |
|---|---|
| MAb1 | 2.5 μM (2.5 × $10^{-6}$M) |
| MAb2 | 185 nM (1.85 × $10^{-7}$M) |
| MAb3 | 6.4 nM (6.4 × $10^{-9}$M) |
| MAb4 | 3.5 nM (3.5 × $10^{-9}$M) |
| MAb5 | 13 pM (1.30 × $10^{-11}$M) |
| MAb6 | 0.6 nM (6.38 × $10^{-10}$M) |
| MAb7 | 58 pM (5.84 × $10^{-11}$M) |
| MAb8 | 0.1 nM (1.08 × $10^{-10}$M) |
| MAb10 | 3.6 nM (3.62 × $10^{-9}$M) |
| MAb11 | 0.3 nM (3.12 × $10^{-10}$M) |
| MAb12 | 0.4 nM (4.43 × $10^{-10}$M) |
| MAb13 | 0.6 nM (6.12 × $10^{-10}$M) |
| MAb14 | 6.8 pM (6.86 × $10^{-12}$M) |
| MAb15 | 0.2 nM (2.11 × $10^{-10}$M) |
| MAb16 | 0.2 nM (2.78 × $10^{-10}$M) |
| MAb17 | 8.3 nM (8.29 × $10^{-9}$M) |
| MAb18 | 1.2 nM (1.24 × $10^{-9}$M) |
| MAb19 | 0.7 nM (7.79 × $10^{-10}$M) |
| MAb20 | 0.2 nM (2.47 × $10^{-10}$M) |
| MAb21 | 3.9 nM (3.90 × $10^{-9}$M) |
| MAb22 | 5 nM (4.94 × $10^{-9}$M) |
| MAb23 | 0.4 μM (3.99 × $10^{-7}$M) |

An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 4.

As noted in TABLES 2A & 2B, several N-terminal and C-terminal monoclonal anti-hPG antibodies have been identified. All of these antibodies are specific for hPG, and, with the exception of MAb14, all exhibited neutralizing activity in tests with colorectal cancer cells. Several of the hybridomas useful for obtaining the antibodies were deposited on Oct. 6, 2010 with the Collection Nationale de Cultures de Microorganisms (CNCM) at 25, Rue du Docteur Rox F-75724 PARIS CEDEX 15, FRANCE in accordance with the Treaty of Budapest. The designated names of the hybridomas producing anti-hPG MAbs1-23 and the depository registration numbers of those hybridomas deposited are provided in TABLES 2A & 2B. In addition, for several of the antibodies, the amino acid sequences of their variable heavy chains ($V_H$), variable light chains ($V_L$), $V_L$ complementarity determining regions (CDRs) and $V_H$ CDRs have been determined. These amino acid sequences, and the shorthand nomenclature used to reference them throughout the disclosure, are also provided in TABLES 2A & 2B. Briefly, murine heavy and light chain variable domains are referred to herein as $mV_H$ and $mV_L$ followed by the number of the corresponding monoclonal antibody, for example $mV_H.3$ and $mV_L.3$ for the variable light and variable heavy chains of anti-hPG MAb3, respectively. Similarly, human heavy and light chain variable domains are referred to herein as $hV_H$ and $hV_L$ followed by the number of the corresponding monoclonal antibody. The three variable heavy chain CDRs and three variable light chain CDRs are referred to as $V_H$ CDR 1, 2, or 3, and $V_L$CDR 1, 2, or 3, respectively, followed by the number of the specific anti-hPG monoclonal antibody. For example, $V_H$ CDR 1 of MAb3 is denoted $V_H$ CDR 1.3 and $V_L$ CDR 1 of MAb3 is denoted $V_L$ CDR 1.3. $V_H$ CDR 2 of MAb3 is denoted $V_H$ CDR 2.3, and $V_L$ CDR 2 of MAb3 is denoted $V_L$ CDR 2.3.

It is expected that corresponding CDRs and/or $V_H$ and $V_L$ chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific non-limiting example to illustrate the various combinations possible, such an antibody could include in its $V_L$ chain, CDRs 1 and 2 of MAb5 ($V_L$ CDR 1.5 and $V_L$ CDR 2.5, respectively) and CDR 3 of MAb6 ($V_L$ CDR 3.6), and in its $V_H$ chain, CDR 1 of MAb6 ($V_H$ CDR 1.6) and CDRs 2 and 3 of MAb5 ($V_H$ CDR 2.5 and $V_H$ CDR 3.5, respectively). Amino acid sequences of CDRs of antibodies (also known as hypervariable regions) produced by hybridomas that have been deposited can be obtained using conventional means.

As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The anti-PG antibodies described herein may contain modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., 1987, *Sequences of Proteins of Immunological Interest*, National Institute of Health, Bethesda, Md.). As used herein, numbering of immunoglobulin amino acid residues is done according to the immunoglobulin amino acid residue numbering system of Kabat et al., unless otherwise indicated.

With reference to TABLE 2A, specific embodiments of N-terminal anti-hPG antibodies useful in the methods and kits described herein include, but are not limited to, the following:

(a) antibodies having $V_L$ CDRs that correspond in sequence to the $V_L$ CDRs of MAb1, MAb2, MAb3, MAb4, MAb15, MAb16, MAb17, MAb18, MAb19 or MAb20, and $V_H$ CDRs that correspond in sequence to the $V_H$ CDRs of MAb1, MAb2, MAb3, MAb4, MAb15, MAb16, MAb17, MAb18, MAb19 or MAb20;

(b) antibodies having $V_L$ CDRs and $V_H$ CDRs that correspond in sequence to the $V_L$ and $V_H$ CDRs of MAb1, MAb2, MAb3, MAb4, MAb15, MAb16, MAb17, MAb18, MAb19 or MAb20;

(c) antibodies in which:
  (i) $V_L$ CDR 1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("$V_L$ CDR 1.19"; SEQ ID NO:51);
  (ii) $V_L$ CDR 2 is selected from KVS ("$V_L$ CDR 2.3" or "$V_L$ CDR 2.4"; SEQ ID NO:5), LVS ("$V_L$ CDR 2.16"; SEQ ID NO:53), and VKKDGSH ("$V_L$ CDR 2.19"; SEQ ID NO:54);
  (iii) $V_L$ CDR 3 is selected from FQGSHVPFT ("$V_L$ CDR 3.3"; SEQ ID NO:6), SQSTHVPPT ("$V_L$ CDR 3.4"; SEQ ID NO:11), WQGTHSPYT ("$V_L$ CDR 3.16"; SEQ ID NO:57), and GVGDAIKGQSVFV ("$V_L$ CDR 3.19"; SEQ ID NO:58);
  (iv) $V_H$ CDR 1 is selected from GYIFTSYW ("$V_H$ CDR 1.3"; SEQ ID NO:1), GYTFSSSW ("$V_H$ CDR 1.4"; SEQ ID NO:7), GYTFTSYY ("$V_H$ CDR 1.16"; SEQ ID NO:39), and GYSITSDYA ("$V_H$ CDR 1.19"; SEQ ID NO:40);
  (v) $V_H$ CDR 2 is selected from FYPGNSDS ("$V_H$ CDR 2.3"; SEQ ID NO:2), FLPGSGST ("$V_H$ CDR 2.4"; SEQ ID NO:8), INPSNGGT ("$V_H$ CDR 2.16"; SEQ ID NO:43), and ISFSGYT ("$V_H$ CDR 2.19"; SEQ ID NO:44); and
  (vi) $V_H$ CDR 3 is selected from TRRDSPQY ("$V_H$ CDR 3.3"; SEQ ID NO:3), ATDGNYDWFAY ("$V_H$ CDR 3.4" SEQ ID NO:9), TRGGYYPFDY ("$V_H$ CDR 3.16"; SEQ ID NO:47), and AREVNYGDSYHFDY ("$V_H$ CDR 3.19"; SEQ ID NO:48);

(d) antibodies having a $V_L$ that corresponds in sequence to the $V_L$ f MAb1, MAb2, MAb3, MAb4, MAb15, MAb16, MAb17, MAb18, MAb19 or MAb20 and a $V_H$ that corresponds in sequence to the $V_H$ of MAb1, MAb2, MAb3, MAb4, MAb15, MAb16, MAb17, MAb18, MAb19 or MAb20; and (e) antibodies having a $V_L$ and a $V_H$ that corresponds in sequence to the $V_L$ and $V_H$ of MAb1, MAb2, MAb3, MAb4, MAb15, MAb16, MAb17, MAb18, MAb19 or MAb20.

With reference to TABLE 2B, specific embodiments of C-terminal anti-hPG antibodies useful in the methods and kits described herein include, but are not limited to, the following:

(a) antibodies having $V_L$ CDRs that correspond in sequence to the $V_L$ CDRs of MAb5, MAb6, MAb7, MAb8, MAb9, MAb10, MAb11, MAb12, MAb13, MAb14, MAb21, MAb22 or MAb23 and $V_H$ CDRs that correspond in sequence to the $V_H$ CDRs of MAb5, MAb6, MAb7, MAb8, MAb9, MAb10, MAb11, MAb12, MAb13, MAb14, MAb21, MAb22 or MAb23;

(b) antibodies having $V_L$ CDRs and $V_H$ CDRs that correspond in sequence to the $V_L$ and $V_H$ CDRs of MAb5, MAb6, MAb7, MAb8, MAb9, MAb10, MAb11, MAb12, MAb13, MAb14, MAb21, MAb22 or MAb23;

(c) antibodies in which:
  (i) $V_L$ CDR 1 is selected from KSLRHTKGITF ("$V_L$ CDR 1.8"; SEQ ID NO:49) and QSLLDSDGKTY ("$V_L$ CDR 1.13"; SEQ ID NO:50);
  (ii) $V_L$ CDR 2 is selected from QMS ("$V_L$ CDR 2.8"; SEQ ID NO:52) and LVS ("$V_L$ CDR 2.13"; SEQ ID NO:53);
  (iii) $V_L$ CDR 3 is selected from AQNLELPLT ("$V_L$ CDR 3.8"; SEQ ID NO:55) and WQGTHFPQT ("$V_L$ CDR 3.13"; SEQ ID NO:56);
  (iv) $V_H$ CDR 1 is selected from GFTFTTYA ("$V_H$ CDR 1.8"; SEQ ID NO:37) and GFIFSSYG ("$V_H$ CDR 1.13"; SEQ ID NO:38);
  (v) $V_H$ CDR 2 is selected from ISSGGTYT ("$V_H$ CDR 2.8"; SEQ ID NO:41) and INTFGDRT ("$V_H$ CDR 2.13"; SEQ ID NO:42); and
  (vi) $V_H$ CDR 3 is selected from ATQGNYSLDF ("$V_H$ CDR 3.8"; SEQ ID NO:45) and ARGTGTY ("$V_H$ CDR 3.13"; SEQ ID NO:46);

(d) antibodies having a $V_L$ that corresponds in sequence to the $V_L$ of MAb5, MAb6, MAb7, MAb8, MAb9, MAb10, MAb11, MAb12, MAb13, MAb14, MAb21, MAb22or MAb23 and a $V_H$ that corresponds in sequence to the $V_H$ of MAb5, MAb6, MAb7, MAb8, MAb9, MAb10, MAb11, MAb12, MAb13, MAb14, MAb21, MAb22 or MAb23; and (e) antibodies having a $V_L$ and a $V_H$ that correspond in sequence to the $V_L$ and $V_H$ that correspond in sequence to the $V_L$ and $V_H$ of MAb5, MAb6, MAb7, MAb8, MAb9, MAb10, MAb$_{11}$1, MAb12, MAb13, MAb14, MAb21, MAb22 or MAb23.

As will be appreciated by skilled artisans, anti-hPG antibodies useful in the diagnostic methods can be of any origin, including, for example, mammalian (e.g., human, primate, rodent, goat or rabbit), non-mammalian, or chimeric in nature (derived from more than one species of origin). Antibodies suitable for therapeutic uses in animals, including humans, are preferably derived from the same species intended to be treated, or have been modified or designed to be non-immunogenic or have reduced immunogenicity in the animal being treated. A specific class of anti-hPG antibodies useful for therapeutic uses in humans is the class of humanized antibodies, discussed in more detail, below. Anti-hPG antibodies useful in the methods and kits described herein can also be of, or derived from, any isotype, including, for example, IgA (e.g., IgA1 or IgA2), IgD, IgE, IgG (e.g., IgG1, IgG2, IgG3 or IgG4) or IgM. Anti-hPG antibodies designed for therapeutic uses are preferably of the IgG isotype.

In some embodiments, anti-hPG antibodies useful for therapeutic methods described herein are humanized. In general, humanized antibodies comprise substantially all of at least one, and typically two, variable domains, in which all or substantially all of the CDR regions correspond to those of a non-human immunoglobulin and all or substantially all of the framework regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods for humanizing antibodies, including methods for designing humanized antibodies, are well-known in the art. See, e.g., Lefranc et al., 2003, Dev. Comp. Immunol. 27:55-77; Lefranc et al., 2009, Nucl. Acids Res. 37:D1006-1012; Lefranc, 2008, Mol. Biotechnol. 40: 101-111; Riechmann et al., 1988, Nature 332:323-7; U.S. Pat. Nos. 5,530,101, 5,585,089, 5,693,761, 5,693,762 and 6,180,370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814; Roguska et al., 1994, Proc. Natl. Acad. Sci. 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in TABLE 2A and the various C-terminal anti-hPG monoclonal antibodies provided in TABLE 2B, can be obtained using these well-known methods. Projected sequences for humanized $V_L$ and $V_H$ chains of selected anti-hPG antibodies are provided in TABLES 2A and 2B. Specific examples of humanized antibodies include antibodies comprising:

(a) any three $V_L$ CDRs and any three $V_H$ CDRs disclosed herein;

(b) a heavy chain variable region comprising an amino acid sequence corresponding to SEQ ID NO:21 and a light chain variable region comprising an amino acid sequence corresponding to SEQ ID NO:22;

(c) a heavy chain variable region comprising an amino acid sequence corresponding to SEQ ID NO:23 and a light chain variable region comprising an amino acid sequence corresponding to SEQ ID NO:24;

(d) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(e) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(f) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (g) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 5.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming an hPG:labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 5.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 5, by at least 50%, at a test antibody concentration in the range of 0.01-100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable.

Skilled artisans will appreciate that is some contexts, for example, diagnostic and monitoring contexts, it may be desirable to label the anti-PG antibodies. Such labels are useful for detection and quantification. Suitable labels are well known in the art, and can be "direct" in that they are directly observable or detectable (for example, fluorophores or radioisotopes) or "indirect" in that they interact with something else that produces and observable or detectable signal (for example, an enzyme that acts on a substrate to produce a detectable signal, or a binding molecule such as biotin that binds a labeled, streptavidin molecule). Numerous labeling systems, as well as means for labeling antibodies with them, are known in the art, and are contemplated for use herein.

Although the various anti-hPG antibodies useful in the methods described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')2, Fab, Fv, vIgG, scFv fragments and surrobodies. Unless specified otherwise, the term "antibody" as used herein is intended to include all forms of antibodies and "antibody-like" surrogate molecules, including single chain antibodies, surrobodies and binding fragments. Antibodies having structures typical of naturally occurring antibodies are referred to herein as "native antibodies."

7.7 Methods of Producing Anti-PG Antibodies

Anti-PG antibodies useful in the methods described herein may be obtained using standard, well-known methods. To express anti-PG antibodies useful in the methods described herein, DNAs encoding partial or full-length light and heavy chains are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-PG antibody light or heavy chain sequences, the expression vector can already carry antibody constant region sequences. For example, one approach to converting the anti-PG antibody $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, *Gene Expression Technology: Methods in Enzymology* 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies described herein in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR⁻CHO cells, described in Urlaub & Chasin, 1980, Proc. Natl. Acad. Sci. USA 77:4216-4220, used with a DHFR selectable marker, e.g., as described in Kaufman & Sharp, 1982, Mol. Biol. 159:601-621), NSO myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as $F_{ab}$ fragments or $scF_v$ molecules. It is understood that variations on the above procedure are within the scope of the present disclosure. For example, it can be desirable to transfect a host cell with DNA encoding either the light chain or the heavy chain (but not both) of an anti-PG antibody described herein.

Recombinant DNA technology can also be used to remove some or all of the DNA encoding either or both of the light and heavy chains that is not necessary for binding to PG. The molecules expressed from such truncated DNA molecules are also useful in the methods described herein.

For recombinant expression of an anti-PG antibody, the host cell can be co-transfected with two expression vectors, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Anti-PG antibodies can also be produced by chemical synthesis (e.g., by the methods described in *Solid Phase Peptide Synthesis,* 2nd ed., 1984 The Pierce Chemical Co., Rockford, Ill.). Variant antibodies can also be generated using a cell-free platform (see, e.g., Chu et al., 2001, Biochemia No. 2 (Roche Molecular Biologicals)).

Once an anti-PG antibody has been produced by recombinant expression or synthetic means, it can be purified by any method known in the art for purification of an immunoglobulin molecule, for example, by chromatography (e.g., ion exchange, affinity, particularly by affinity for PG after Protein A or Protein G selection, and sizing column chromatography), centrifugation, differential solubility, or by any other standard technique for the purification of proteins. Further, the anti-PG antibodies or binding fragments thereof can be fused to heterologous polypeptide sequences described herein or otherwise known in the art to facilitate purification.

8. EXAMPLES 8.1 Example 1: Quantification of Plasma or Serum PG Levels

Plasma and/or serum levels of PG can be conveniently determined using the following assay. 96-well microtiter plates are coated with between 0.5 and 10 µg/mL of a C-terminal anti-hPG antibody, for example, a rabbit C-terminal anti-hPG polyclonal antibody, or a C-terminal anti-hPG antibody described herein, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 µg/mL of an N-terminal anti-hPG antibody, for example, a polyclonal N-terminal anti-hPG antibody or an N-terminal monoclonal anti-hPG antibody as described herein, coupled to horseradish peroxidase (HRP) (see, Nakane et al., 1974, J. Histochem. Cytochem. 22(12):1084-1091) for 30 minutes at 21° C. Plates are then washed three times in PBS-Tween (0.05%) and HRP substrate is added for 15 minutes at 21° C. The reaction is stopped by added 100 µL of 0.5M sulfuric acid and an optical density measurement is taken at 405 nm. Test sample hPG levels are determined by comparison to a standard curve constructed from the measurements derived from the hPG reference standard.

8.2 Example 2: ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 µL blocking solution (PBS, 0.1% Tween-20, 0.1% Bovine Serum Albumin or casein hydrolysate) per well. After blocking, the wells are washed three times and the antibody to be assayed (test antibody) is added. 100 µL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3× 100 µL wash solution, as noted above), with blocking solution containing a secondary antibody, a goat anti-mouse IgG (Fc) antibody coupled to horseradish peroxidase. After a 1-hour incubation with secondary antibody, 100 µL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 µL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

8.3 Example 3: Assay for Assessing Neutralizing Activity of Anti-hPG Antibodies

A specific test for assessing whether a specific anti-hPG antibody is neutralizing can be performed as follows. LS174T cells are seeded in 6 wells of a 6-well plate, at approximately 50,000 cells per well. Cells are then treated at 12-hour intervals for 48 hours with the test anti-hPG antibody or a control antibody, at antibody concentrations of about 5 µg/mL. A test antibody is defined as neutralizing in the assay, if the number of cells treated with the test antibody shows a statistically significant reduction of at least 10% in the number of surviving cells compared to the number of cells treated with a control, non-specific antibody, using a two-tailed Mann-Whitney test (with differences considered as significant when $p<0.05$). Total cell numbers are corrected for the number of cells at the start of the treatment period, referred to as $T_0$.

8.4 Example 4: Assay for Assessing Affinity of an Anti-hPG Antibody

Affinity constants of anti-hPG antibodies can be measured using the Proteon Technique (BioRad), according to Nahshol et al., 2008, Analytical Biochemistry 383:52-60, hereby incorporated by reference in its entirety. Briefly, for murine anti-PG antibodies, an anti-mouse IgG antibody (50 µg/ml) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 µg/ml). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

8.5 Example 5: Assay for Assessing Competitive Binding With a Reference Anti-hPG Antibody A specific assay for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N- or C-terminal region of hPG that differs from the epitope recognized by the biotinylated reference anti-hPG antibody), at a concentration to be chosen within the range of 1-10 μg/ml, overnight at 4° C. (0.1 to 1 μg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/ml streptavidin-HRP for 1 hr at 22° C., followed by incubation with a chemiluminescent substrate for horseradish peroxidase for 5 minutes at 22° C., and then quantifying the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody.

In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$ which is calculated according to the following formula:

$$K_i = IC_{50}/[1+(\text{reference anti-hPG Ab concentration}/K_D^{reference\ anti-hPG\ Ab})]$$

where "$IC_{50}$" is the concentration of test antibody that yields a 50% reduction in binding of the reference antibody and $K_D^{reference\ anti-hPG\ Ab}$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

8.6 Example 6: Detection of Serum PG In Samples from Patients With Familial Adenomatous Polyposis This example shows that elevated serum PG levels can be correlated with the presence of polyps in individual with FAP.

8.6.1 Methods

Serum PG levels were quantified as described in Example 1 in samples from 6 patients with Familial Adenomatous Polyposis. Serum samples were obtained from patients with the following characteristics:

- Two individuals (A and B), both older than 55, having previously undergone colectomy, regularly monitored by endoscopy, in whom no polyps have been detected since surgery.
- One individual (C), aged 30, having previously undergone colectomy and follow up surgery to remove further polyps. The individual had surgery several months before the blood sample was collected.
- One individual (D), aged 27, having previously undergone colectomy, presenting with multiple polyps in the small intestine (but no cancer) at the time the blood sample was collected.
- One individual (E), aged 52, having previously undergone colectomy presenting with multiple polyps in the rectum at the time a blood sample was collected.
- One individual (F), aged 10, presenting with multiple colorectal polyps at the time a blood sample was collected.

8.6.2 Results

Results shown Table 5 below are expressed as mean PG concentration±standard deviation (pM):

TABLE 5

| Patient | Mean PG Concentration (pM) ± s.d. |
|---|---|
| A | 6.9 ± 3.3 |
| B | 0.0 |
| C | 0.0 |
| D | 167.5 ± 43.0 |
| E | 351.85 ± 96.0 |
| F | 233 ± 11.3 |

Results indicate that PG levels are particularly elevated in individuals bearing a high number of polyps at the time of sampling. In comparison, patients who have undergone surgery display very low or undetectable levels of PG.

8.7 Example 7: Detection of Serum PG In Samples From Patients With Pre-Cancerous Sporadic Adenomatous Polyps This example demonstrates that more than twenty-five percent of individuals with sporadic adenomatous polyposis have increased serum PG levels.

8.7.1 Methods

PG levels were measured in two different sample sets: a first set of samples obtained from twenty-five individuals having multiple adenomatous polyps, similar to the number that would be found in subjects with FAP, and a second set of samples from a plasma bank, collected from 104 individuals ranging in age from 45 to 65 years. Plasma progastrin levels were quantified using an ELISA assay, as described above in Example 1.

8.7.2 Results

23% (12/52) of subjects with adenomatous polyps studied had progastrin levels above 50 pM. By comparison, 16.3% (17/104) of subjects in from the blood bank group had PG levels above 50 pM. The medical history of the individuals whose samples were banked is unknown. Healthy individuals have low levels of PG, not typically exceeding 50 pM. See, e.g., Siddheshwar et al., 2001, "Plasma levels of progastrin but not amidated gastrin or glycine extended gastrin are elevated in patients with colorectal carcinoma," *Gut* 48:47-52. Levels above 50 pM are thought to be indicative of an underlying pathology.

Almost one quarter of the individuals in whom polyps were found also had elevated PG levels. This is consistent with the observation that about 20% of sporadic adenomatous polyps develop into malignant tumors, a transformation that is thought to be accompanied by elevated PG levels. Therefore, elevated PG levels in the presence of adenomatous polyps can serve as a useful metric in identifying patients for further follow-up or for prophylactic anti-PG treatment.

With respect to the samples from the plasma bank, it is likely that some or all of the banked samples with PG levels above 50 pM came from individuals with underlying conditions that caused elevated PG levels. Use of appropriately screened control samples would likely show a greater difference between the percentage of individuals with sporadic adenomatous polyps and those without polyps who have PG levels above 50 pM.

8.8 Example 8: Anti-PG Compositions Prevent Tumor Development in A Mouse Model of FAP This example demonstrates the ability of anti-hPG antibodies to prevent the formation of tumors in vivo.

8.8.1 Methods

Transgenic mice carrying a mutation in an allele of the Adenomatous Polyposis Coli (APC) gene similar to that found in individuals with Familial Adenomatous Polyposis (FAP), were treated with an anti-hPG antibody. These mice, referred to as APCΔ14 mice, spontaneously develop tumors in their intestines when the second (wild type) APC allele is lost via a "loss of heterozygocity" (LOH) mechanism, (Colnot et al., 2004, "Colorectal cancers in a new mouse model of familial adenomatous polyposis: influence of genetic and environmental modifiers," *Lab Investigation* 84:1619-1630). The first detectable tumors can be found around 2 months of age, and by 3.5 months, the number of tumors is generally around 15-20. These tumors have been shown to produce progastrin.

Four-month-old APCΔ14 mice were treated twice a week for six weeks with either a control polyclonal antibody antibody—a rabbit anti-human IgG antiserum (Jackson ImmunoResearch (reference no. 309-005-0089)—or an anti-PG polyclonal antibody, raised against (1) an N-terminal peptide and (2) a C-terminal peptide as described in Hollande et al., WO 07/135542, by intra-peritoneal injection at a dose of 9 mg/kg. The mice were weighed once a week. At the end of the six-week treatment regimen, their intestines were photographed, the total number of tumors counted. There were six mice in the treatment and the control group. Genotyping identified two mice from the control group that did not carry the expected heterozygous APC mutation, and were excluded from the experiment.

8.8.2 Results

Results are shown below in Table 6. Mice treated with control antibody exhibited a total of 125 tumors, with 31.25 tumors on average per mouse. Anti-PG treated mice has 46 total tumors or, on average, 7.6 tumors per mouse. This difference is statistically significant (Mann-Whitney test, P=0.0095).

TABLE 6

| Treatment (no. of mice) | Number of tumors per mouse | | | | | |
|---|---|---|---|---|---|---|
| Control PAb (4) | | 23 | 48 | 28 | | 26 |
| Anti-hPG PAb (6) | 2 | 16 | 15 | 9 | 2 | 2 |

Results indicate that the number of tumors found in four out the six animals treated with anti-progastrin antibodies falls below the average number of fifteen to twenty tumors generally found in APCΔ14 mice at 3.5 months of age. See, Table 6 below. These data indicate that treatment with anti-progastrin antibodies prevents new tumors from developing in these animals.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of inhibiting the formation of a progastrin-dependent gastrointestinal cancer in a human subject, comprising administering to a human subject an amount of an anti-PG monoclonal antibody sufficient to provide a therapeutic benefit, wherein said monoclonal antibody is selected from the group consisting of:

a monoclonal antibody comprising $V_H$ CDRs comprising amino acid sequences of $V_H$ CDR 1.8 (SEQ ID NO:37), $V_H$ CDR 2.8 (SEQ ID NO:41), $V_H$ CDR 3.8 (SEQ ID NO:45) and $V_L$ CDRs comprising amino acid sequences of $V_L$ CDR 1.8 (SEQ ID NO:49), $V_L$ CDR 2.8 (SEQ ID NO:52), and $V_L$ CDR 3.8 (SEQ ID NO:55);

a monoclonal antibody comprising $V_H$ CDRs comprising amino acid sequences of $V_H$ CDR 1.13 (SEQ ID NO:38), $V_H$ CDR 2.13 (SEQ ID NO:42), $V_H$ CDR 3.13 (SEQ ID NO:46) and $V_L$ CDRs comprising amino acid sequences of $V_L$ CDR 1.13 (SEQ ID NO:50), $V_L$ CDR 2.13 (SEQ ID NO:53), and $V_L$ CDR 3.13 (SEQ ID NO:56), a monoclonal antibody produced by a hybridoma deposited on Oct. 6, 2010 with the Collection Nationale de Cultures de Microorganisms (CNCM) under reference I-4371;

a monoclonal antibody produced by a hybridoma deposited on Oct. 6, 2010 with the Collection Nationale de Cultures de Microorganisms (CNCM) under reference I-4372;

a monoclonal antibody produced by a hybridoma deposited on Oct. 6, 2010 with the Collection Nationale de Cultures de Microorganisms (CNCM) under reference I-4373;

a monoclonal antibody produced by a hybridoma deposited on Oct. 6, 2010 with the Collection Nationale de Cultures de Microorganisms (CNCM) under reference I-4374;

a monoclonal antibody produced by a hybridoma deposited on Oct. 6, 2010 with the Collection Nationale de Cultures de Microorganisms (CNCM) under reference I-4375;

wherein the subject has a mutation in the APC gene associated with adenomatous polyposis; and wherein the subject has familial adenomatous polyposis.

2. The method of claim 1 in which the anti-hPG monoclonal antibody is a humanized anti-hPG monoclonal antibody.

3. The method of claim 1 in which the anti-hPG monoclonal antibody is a C-terminal anti-hPG monoclonal antibody.

4. The method of claim 3 in which the C-terminal anti-hPG monoclonal antibody binds an epitope comprising a sequence selected from the group consisting of FGRR (SEQ ID NO:33) and MDFGR (SEQ ID NO:34).

5. The method of claim 3 in which the C-terminal anti hPG monoclonal antibody is raised against an immunogen comprising a peptide having the sequence QGPWLEEEEE-AYGWMDFGRRSAEDEN (SEQ ID NO:27).

6. The method of claim 1, in which the anti-hPG monoclonal antibody is administered adjunctive to surgical resection of tissue comprising adenomatous polyps.

7. The method of claim 1, in which the anti-hPG monoclonal antibody is administered adjunctive to chemotherapy.

8. The method of claim 1, in which the anti-hPG monoclonal antibody is administered adjunctive to treatment with a non-steroidal anti-inflammatory drug.

\* \* \* \* \*

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
1               5

<210> SEQ ID NO 8

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80
```

```
Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
    50                  55                  60

Lys Gly Lys Ala Thr Phe Thr Ala Asp Thr Ser Ser Asp Thr Ala Tyr
65                  70                  75                  80

Met Leu Leu Ser Ser Leu Thr Ser Glu Asp Ser Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 15
```

<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Val Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
            100                 105                 110
```

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(345)

<400> SEQUENCE: 16

```
gag gtt cag ctc cag cag tct ggg act gtg ctg gca agg cct ggg gct      48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac      96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att     144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc     192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac     240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt     288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca     336
Thr Arg Arg Asp Ser Pro Gln Tyr Trp Gly Gln Gly Thr Thr Leu Thr
            100                 105                 110 gtc tcc tca                                                         345
Val Ser Ser
        115
```

<210> SEQ ID NO 17
<211> LENGTH: 336

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt    96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt   288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa   336
Ser His Val Pro Phe Thr Phe Gly Gly Gly Thr Lys Leu Glu Ile Lys
            100                 105                 110
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(354)

<400> SEQUENCE: 18

```
cag gtt cag ttg cag cag tct gga gct gag ctg atg aag cca ggg gcc    48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc    96
Ser Val Lys Ile Ser Cys Lys Ala Thr Gly Tyr Thr Phe Ser Ser Ser
            20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
        35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
    50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
```

```
                  100                 105                 110
ctg gtc act gtc tct gca                                                354
Leu Val Thr Val Ser Ala
        115

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 19 gat ctt gtg atg acc caa act cca ctc tcc ctg cct gtc agt ctt gga      48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt      96
Asp Gln Ala Ser Ile Ser Cys Arg Ser Ser Gln Ser Leu Val His Ser
            20                  25                  30 agt gga gtc acc tat tta cat tgg tac ctg cag aag cca ggc cag tct     144
Ser Gly Val Thr Tyr Leu His Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt     288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa     336
Thr His Val Pro Pro Thr Phe Gly Ser Gly Thr Lys Leu Glu Ile Lys
            100                 105                 110

<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15

<210> SEQ ID NO 27
<211> LENGTH: 26

<212> TYPE: PRT
<213> ORGANISM: Homo sapiens

<400> SEQUENCE: 27

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 28
<211> LENGTH: 5
<212> TYPE: PRT
<213> ORGANISM: Homo sapiens

<400> SEQUENCE: 28

Asp Ala Pro Leu Gly
1               5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
1

<210> SEQ ID NO 34

```
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens

<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Gln Gly Asn Tyr Ser Leu Asp Phe
1               5                   10

```
<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Gly Gly Tyr Tyr Pro Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Glu Val Asn Tyr Gly Asp Ser Tyr His Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Arg His Thr Lys Gly Ile Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Leu Leu Asp Ser Asp Gly Lys Thr Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

```
Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5

<210> SEQ ID NO 57
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gln Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
```

```
                50                  55                  60
Lys Gly Arg Phe Thr Ile Ser Arg Asp Asn Ala Lys Asn Thr Leu Tyr
 65                  70                  75                  80

Leu Gln Met Thr Ser Leu Lys Ser Glu Asp Thr Ala Ile Tyr Tyr Cys
                    85                  90                  95

Ala Arg Gly Thr Gly Thr Tyr Trp Gly Gln Gly Thr Thr Leu Thr Val
                100                 105                 110

Ser Ser

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Tyr Met Tyr Trp Val Lys Gln Arg Pro Gly Gln Gly Leu Glu Trp Ile
            35                  40                  45

Gly Glu Ile Asn Pro Ser Asn Gly Gly Thr Asn Phe Asn Glu Lys Phe
        50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Thr Arg Gly Gly Tyr Tyr Pro Phe Asp Tyr Trp Gly Gln Gly Thr Thr
                100                 105                 110

Leu Thr Val Ser Ser
            115

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Phe Ser Gly Tyr Thr Ser Tyr Asn Pro Ser Leu
        50                  55                  60

Lys Ser Arg Ile Ser Val Thr Arg Asp Thr Ser Arg Asn Gln Phe Phe
 65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
                100                 105                 110
```

```
Gln Gly Thr Ile Val Thr Val Ser Ser
        115                 120
```

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Asp Ile Val Met Thr Gln Ala Ala Ser Ser Asn Pro Val Thr Leu Gly
1               5                   10                  15

Thr Ser Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Leu Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Ser Leu Lys Pro Pro Lys Tyr Val Met
        35                  40                  45

Glu Val Lys Lys Asp Gly Ser His Ser Thr Gly His Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat      96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc     144

```
Ala Met Ser Trp Val Arg Gln Thr Pro Glu Lys Arg Leu Glu Trp Val
            35                  40                  45 gca acc att agt agt ggt ggt act tac acc tac tat cca gac agt gtg        192
Ala Thr Ile Ser Ser Gly Gly Thr Tyr Thr Tyr Tyr Pro Asp Ser Val
 50                  55                  60 aag ggt cga ttc acc atc tcc aga gac aat gcc aag aac gcc cta tac        240
Lys Gly Arg Phe Thr Ile Ser Arg Asp Asn Ala Lys Asn Ala Leu Tyr
 65                  70                  75                  80 ctg caa atg agc agt ctg agg tct gag gac acg gcc atg tat tac tgt        288
Leu Gln Met Ser Ser Leu Arg Ser Glu Asp Thr Ala Met Tyr Tyr Cys
                 85                  90                  95 gca aca cag ggg aat tac tct ttg gac ttc tgg ggc caa ggc acc tct        336
Ala Thr Gln Gly Asn Tyr Ser Leu Asp Phe Trp Gly Gln Gly Thr Ser
            100                 105                 110 ctc aca gtc tcc tca                                                    351
Leu Thr Val Ser Ser
            115

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68 gag gtg cag ctg gtg gag tct ggg gga ggc ttg gtg cag cct gga ggg         48
Glu Val Gln Leu Val Glu Ser Gly Gly Gly Leu Val Gln Pro Gly Gly
  1               5                  10                  15 tcc ctg aaa ctc tcc tgt gca gcc tct gga ttc att ttc agt agc tat         96
Ser Leu Lys Leu Ser Cys Ala Ala Ser Gly Phe Ile Phe Ser Ser Tyr
             20                  25                  30 ggc atg tct tgg gtt cgc cag tct cca gac agg agg ctg gag ttg gtc        144
Gly Met Ser Trp Val Arg Gln Ser Pro Asp Arg Arg Leu Glu Leu Val
         35                  40                  45 gca agt att aat act ttt ggt gat aga acc tat tat cca gac agt gtg        192
Ala Ser Ile Asn Thr Phe Gly Asp Arg Thr Tyr Tyr Pro Asp Ser Val
 50                  55                  60 aag ggc cga ttc acc atc tcc aga gac aat gcc aag aac acc ctg tac        240
Lys Gly Arg Phe Thr Ile Ser Arg Asp Asn Ala Lys Asn Thr Leu Tyr
 65                  70                  75                  80 ctg caa atg acc agt ctg aag tct gag gac aca gcc att tat tac tgt        288
Leu Gln Met Thr Ser Leu Lys Ser Glu Asp Thr Ala Ile Tyr Tyr Cys
                 85                  90                  95 gca aga ggg acc gga acc tac tgg ggc caa ggc acc act ctc aca gtc        336
Ala Arg Gly Thr Gly Thr Tyr Trp Gly Gln Gly Thr Thr Leu Thr Val
            100                 105                 110 tcc tca                                                                342
Ser Ser <210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)
```

<400> SEQUENCE: 69

```
cag gtc caa ctg cag cag tct ggg gct gaa ctg gtg aag cct ggg gct         48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac         96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att        144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc        192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac        240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt        288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act        336
Thr Arg Gly Gly Tyr Tyr Pro Phe Asp Tyr Trp Gly Gln Gly Thr Thr
            100                 105                 110 ctc aca gtc tcc tca                                                     351
Leu Thr Val Ser Ser
        115
```

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70

```
gat gtg cag ctt cag gag tcg gga cct ggc ctg gtg aaa cct tct cag         48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat         96
Ser Leu Ser Leu Thr Cys Thr Val Thr Gly Tyr Ser Ile Thr Ser Asp
            20                  25                  30 tat gcc tgg aat tgg atc cgg cag ttt cca gga aac aaa ctg gag tgg        144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc        192
Met Gly Tyr Ile Ser Phe Ser Gly Tyr Thr Ser Tyr Asn Pro Ser Leu
    50                  55                  60 aaa agt cga atc tct gtc act cgg gac aca tcc agg aac caa ttc ttc        240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt        288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc        336
Ala Arg Glu Val Asn Tyr Gly Asp Ser Tyr His Phe Asp Tyr Trp Gly
            100                 105                 110 caa ggc acc att gtc aca gtc tcc tca                                    363
Gln Gly Thr Ile Val Thr Val Ser Ser
```

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 71

```
gac att gtg atg acg cag gct gca tcc tct aat cca gtc act ctt gga      48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act      96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct     144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca     192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc     240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat     288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa     336
Leu Glu Leu Pro Leu Thr Phe Gly Ala Gly Thr Lys Leu Glu Leu Lys
            100                 105                 110
```

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 72

```
gat gtt gtg ctg acc cag act cca ctc act ttg tcg gtt acc att gga      48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt      96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct     144
Asp Gly Lys Thr Tyr Leu Asn Trp Leu Leu Gln Arg Pro Gly Gln Ser
        35                  40                  45 cca aag cgc cta atc tat ctg gtg tct aaa ctg gac tct gga gtc cct     192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aaa atc     240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt     288
Ser Arg Val Glu Ala Glu Asp Leu Gly Val Tyr Tyr Cys Trp Gln Gly
```

```
Ser Arg Val Glu Ala Glu Asp Leu Gly Val Tyr Tyr Cys Trp Gln Gly
            85                  90                  95 aca cat ttt cct cag acg ttc ggt gga ggc acc aag ctg gaa atc aaa      336
Thr His Phe Pro Gln Thr Phe Gly Gly Gly Thr Lys Leu Glu Ile Lys
            100                 105                 110

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 73 gat gtt gtg atg acc cag act cca ctc act ttg tcg gtt acc att ggg      48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt      96
Arg Pro Ala Ser Ile Ser Cys Lys Ser Ser Gln Ser Leu Leu Asp Ser
            20                  25                  30 gat gga aag aca tat ttg tat tgg ttg tta cag agg cca ggc cag tct      144
Asp Gly Lys Thr Tyr Leu Tyr Trp Leu Leu Gln Arg Pro Gly Gln Ser
        35                  40                  45 cca aag cgc cta atc tat ctg gtg tct gag ctg gac tct gga gtc cct      192
Pro Lys Arg Leu Ile Tyr Leu Val Ser Glu Leu Asp Ser Gly Val Pro
    50                  55                  60 gac agg atc act ggc agt ggg tcg ggg aca gat ttc aca ctg aag atc      240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga      288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa      336
Thr His Ser Pro Tyr Thr Phe Gly Gly Gly Thr Lys Leu Glu Ile Lys
            100                 105                 110

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74 caa ctt gcg ctc act cag tca tct tca gcc tct ttc tcc ctg gga gcc      48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc      96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg      144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat      192
Glu Val Lys Lys Asp Gly Ser His Ser Thr Gly His Gly Ile Pro Asp
    50                  55                  60
```

```
cgc ttc tct gga tcc agt tct ggt gct gat cgc tac ctc agc att tcc       240
Arg Phe Ser Gly Ser Ser Ser Gly Ala Asp Arg Tyr Leu Ser Ile Ser
 65                  70                  75                  80 aac atc cag cct gaa gat gaa gca ata tac atc tgt ggt gtg ggt gat       288
Asn Ile Gln Pro Glu Asp Glu Ala Ile Tyr Ile Cys Gly Val Gly Asp
                 85                  90                  95 gca att aag gga caa tct gtg ttt gtt ttc ggc ggt ggc acc aag gtc       336
Ala Ile Lys Gly Gln Ser Val Phe Val Phe Gly Gly Gly Thr Lys Val
            100                 105                 110 act gtc cta                                                           345
Thr Val Leu
        115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

```
<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

```
Leu Glu Leu Pro Leu Thr Phe Gly Gly Gly Thr Lys Val Glu Ile Lys
                100                 105                 110
```

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110
```

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gln Gly Thr Thr
            100                 105                 110

Val Thr Val Ser Ser
        115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser

```
                35                  40                  45

Pro Arg Arg Leu Ile Tyr Leu Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Gln Thr Phe Gly Gly Gly Thr Lys Val Glu Ile Lys
                100                 105                 110

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Ser Tyr
                 20                  25                  30

Gly Met Ser Trp Val Arg Gln Ala Pro Gly Lys Gly Leu Glu Trp Val
             35                  40                  45

Ala Ser Ile Asn Thr Phe Gly Asp Arg Thr Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Thr Gly Thr Tyr Trp Gly Gln Gly Thr Leu Val Thr Val
                100                 105                 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu Asp Ser
                 20                  25                  30

Asp Gly Lys Thr Tyr Leu Asn Trp Phe Gln Gln Arg Pro Gly Gln Ser
             35                  40                  45

Pro Arg Arg Leu Ile Tyr Leu Val Ser Lys Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Gln Thr Phe Gly Gly Gly Thr Lys Val Glu Ile Lys
                100                 105                 110
```

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
            115

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met

```
                35                  40                  45
Glu Val Lys Lys Asp Gly Ser His Ser Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
            100                 105                 110

Glu Ile Lys
        115

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

Cys Xaa Xaa Gln Gly Pro Trp Leu Glu Glu Glu Glu Glu Ala Tyr Gly
 1               5                  10                  15

Trp Met Asp Phe Gly Arg Arg Ser Ala Glu Asp Glu Asn
             20                  25

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
 1               5                  10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
 1               5                  10

<210> SEQ ID NO 99
<211> LENGTH: 15
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 99

Gly Gly Gly Gly Ser Gly Gly Gly Ser Gly Gly Gly Gly Ser
1               5                   10                  15

<210> SEQ ID NO 100
<211> LENGTH: 101
<212> TYPE: PRT
<213> ORGANISM: Homo sapiens

<400> SEQUENCE: 100

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
                20                  25                  30

Pro Leu Gly Thr Gly Ala Asn Arg Asp Leu Glu Leu Pro Trp Leu Glu
            35                  40                  45

Gln Gln Gly Pro Ala Ser His His Arg Arg Gln Leu Gly Pro Gln Gly
        50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
                20                  25                  30

Ser His His Arg Arg Gln Leu Gly Pro Gln Gly Pro Pro His Leu Val
            35                  40                  45

Ala Asp Pro Ser Lys Lys Gln Gly Pro Trp Leu Glu Glu Glu Glu Glu
        50                  55                  60

Ala Tyr Gly Trp Met Asp Phe Gly Arg Arg Ser Ala Glu Asp Glu Asn
65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
                20                  25                  30

Asp Phe

<210> SEQ ID NO 103

```
<211> LENGTH: 35
<212> TYPE: PRT
<213> ORGANISM: Homo Sapiens

<400> SEQUENCE: 103

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe Gly
        35

<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Ala Tyr Gly Trp Met Asp
1               5                   10                  15

Phe

<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15

Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```